(12) United States Patent
Anderson et al.

(10) Patent No.: US 7,329,504 B2
(45) Date of Patent: Feb. 12, 2008

(54) METHODS OF PREVENTING OR TREATING CELL MIGRATION MEDIATED CONDITIONS OR DISEASES

(75) Inventors: Richard A. Anderson, Cross Plains, WI (US); Kun Ling, Madison, WI (US); Renee L. Doughman, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/493,489

(22) Filed: Jul. 26, 2006

(65) Prior Publication Data

US 2006/0257848 A1 Nov. 16, 2006

Related U.S. Application Data

(62) Division of application No. 10/606,038, filed on Jun. 25, 2003, now Pat. No. 7,097,993.

(51) Int. Cl.
*C12Q 1/48* (2006.01)
(52) U.S. Cl. .......................................... 435/15; 435/29
(58) Field of Classification Search .................. 435/15, 435/29, 69.2, 194
See application file for complete search history.

(56) References Cited

U.S. PATENT DOCUMENTS

| 4,736,866 | A | 4/1988 | Leder et al. | 800/1 |
|---|---|---|---|---|
| 4,745,051 | A | 5/1988 | Smith et al. | 435/68 |
| 4,870,009 | A | 9/1989 | Evans et al. | 435/70 |
| 4,879,236 | A | 11/1989 | Smith et al. | 435/235 |
| 5,166,320 | A | 11/1992 | Wu et al. | 530/395 |
| 7,097,993 | B2 * | 8/2006 | Anderson et al. | 435/15 |

FOREIGN PATENT DOCUMENTS

| EP | 0 362 179 A3 | 4/1990 |
|---|---|---|
| EP | 0 264 166 B1 | 8/1996 |
| WO | WO 90/13646 | 11/1990 |
| WO | WO 97/19954 | 6/1997 |

OTHER PUBLICATIONS

Ling K. et al. Type I gamma Phosphatidylinositol Phosphate Kinase Targets and Regulates Focal Adhesions. Nature. vol. 420, 89-93, Nov. 2002.*
Anderson et al., "Phosphatidylinositol Phosphate Kinases, a Multifaceted Family of Signaling Enzymes", J. Biological Chemistry 1999 274(15):9907-9910.
Barry et al., "The RhoA-dependent assembly of focal adhesions in Swiss 3T3 cells is associated with increased tyrosine phosphorylation and the recruitment of both pp125FAK and protein kinase C-γ to focal adhesions", Journal of Cell Science 1994 107:2033-2045.
Berditchevski et al., "A Novel Link between Integrins, Transmembrane-4 Superfamily Proteins (CD63 and CD81), and Phosphatidylinositol 4-Kinase", J. Biological Chemistry 1997 272(5):2595-2598.

Burridge et al., "Focal Adhesions, Contractility, and Signaling", Annu. Rev. Cell Dev. Biol. 1996 12:463-519.
Cary et al., "Focal Adhesion Kinase In Integrin-Mediated Signaling", Frontiers in Bioscience 1999 4(d102-113):1-24.
Chong et al., "The Small GTP-Binding Protein Rho Regulates a Phosphatidylinositol 4-Phosphate 5-Kinase in Mammalian Cells", Cell 1994 79:507-513.
Chrzanowska-Wodnicka et al., "Tyrosine phosphorylation is involved in reorganization of the actin cytoskeleton in response to serum of LPA stimulation", Journal of Cell Science 1994 107:3643-3654.
Cobb et al., "Stable Association of $pp60^{src}$ and $pp59^{fyn}$ with the Focal Adhesion-Associated Protein Tyrosine Kinase, $pp125^{FAK}$", Molecular and Cellular Biology 1994 14(1):147-155.
Critchley David R., "Focal adhesions-the cytoskeletal connection", Currrent Opinion in Cell Biology 2000 12:133-139.
DiPaolo et al., "Recruitment and regulation of phosphatidylinositol phosphate kinase type 1γ by the FERM domain of talin", Nature 2002 420:85-93.
Gilmore et al., "Regulation of vinculin binding to talin and actin by phosphatidyl-inositol-4-5-biphosphate", Nature 1996 381:531-535.
Ishihara et al., "Type I Phosphatidylinositol-4-phosphate 5-Kinases", Journal of Biological Chemistry 1996 273(15):8741-8478.
Janney Paul A., "Phosphoinositides and Calcium as Regulators of Cellular Actin Assembly and Disassembly", Annu. Rev. Physiol. 1994 56:169-191.
Kunz et al., "The Activation Loop of Phosphatidylinositol Phosphate Kinases Determines Signaling Specificity", Molecular Cell 2000 5:1-11.
Ling et al., "Type 1γ phosphatidylinositol phosphate kinase targets and regulates focal adhesions", Nature 2002 420:89-93.
Martel et al., "Conformation, Localization, and Integrin Binding of Talin Depend on Its Interaction with Phosphoinositides", J. Biol. Chem. 2001 276(24):21217-21227.
McNamee et al., "Adhesion to Fibronectin Stimulates Inositol Lipid Synthesis and Enhances PDGF-induced Inositol Lipid Breakdown", J. Cell Biology 1993 121:673-678.
Parsons et al., "Focal Adhesion Kinase: a regulator of focal adhesion dynamics and cell movement", Oncogene 2000 19:5606-5613.
Ridley et al., "Signal transduction pathways regulating Rho-mediated stress fibre formation:requirement for a tyrosine kinase", The EMBO Journal 1994 13(11):2600-2610.
Schaller et al., "Autophosphorylation of the Focal Adhesion Kinase, $pp125^{FAK}$, Directs SH2-Dependent Binding of $pp60^{src}$", Molecular and Cellular Biology 1994 14(3):1680-1688.

(Continued)

*Primary Examiner*—Ralph Gitomer
(74) *Attorney, Agent, or Firm*—Licata & Tyrrell P.C.

(57) ABSTRACT

The present invention relates to methods of identifying agents which modulate the activity of PIPKIγ661. Methods of using such agents to prevent or treat a cell migration-mediated condition or disease in a subject are also provided.

1 Claim, 1 Drawing Sheet

OTHER PUBLICATIONS

Schaller Michael D., "Biochemical signals and biological responses elicited by the focal adhesion kinase", Biochmica et Biophysica Acta 1540 2001 1-21.

Schaller et al., "Complex Formation with Focal Adhesion Kinase:A Mechanism to Regulate Activity and Subcellular Localization of Src Kinases", Molecular Biology of the Cell 1999 10:3489-3505.

Schwartz et al., "Networks and crosstalk:integrin signalling spreads", Nature Cell Biology 2002 4:E65-E68.

Steimle et al., "Polyphosphoinositides Inhibit the Interaction of Vinculin with Actin Filaments", Journal of Biological Chemistry 1999 274(26):18414-18420.

* cited by examiner

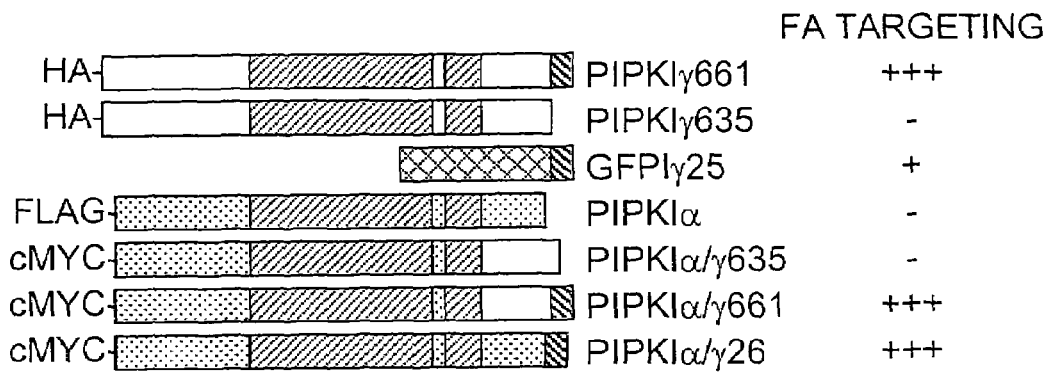
FIG. 1
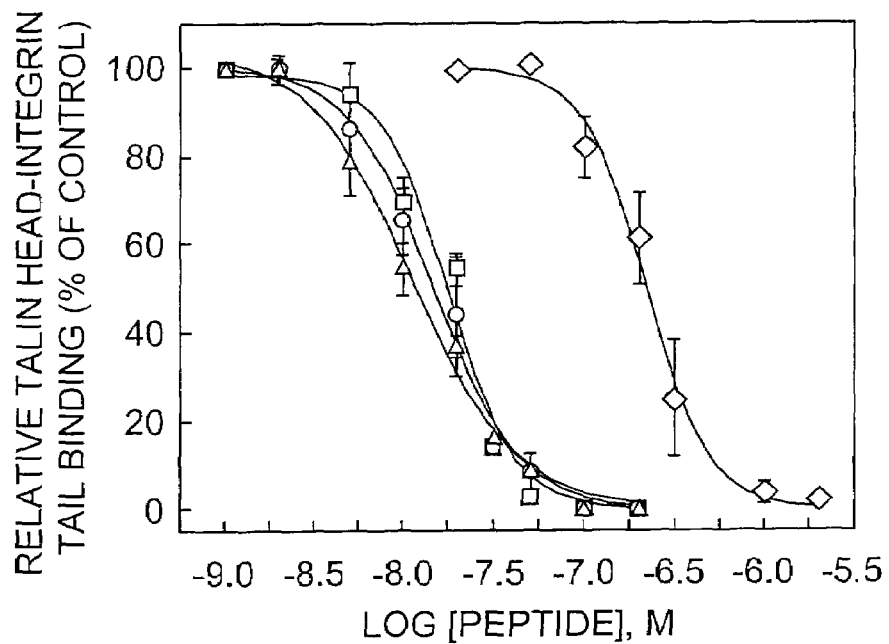
FIG. 2
| PIPKIγ661 | ▭▨▧-PTDERSWVYSPLHYSARPASDGESDT(SEQ ID NO:2) |
| PIPKIγ-W | ▨▧-PTDERS (SEQ ID NO:24) |
| PIPKIγ-Y | ▨▧-PTDERSWVYSPLH (SEQ ID NO:25) |
| PIPKIγ-E | ▨▧-PTDERSWVYSPLHYSARPASDG (SEQ ID NO:26) |
| IγY641F | ▨▧-PTDERSWVFSPLHYSARPASDGESDT(SEQ ID NO:27) |
| IγY649F | ▨▧-PTDERSWVYSPLHFSARPASDGESDT(SEQ ID NO:28) |
| IγY644/649F | ▨▧-PTDERSWVFSPLHFSARPASDGESDT(SEQ ID NO:29) |
FIG. 3

SEQUENCE LISTING

```
<160> NUMBER OF SEQ ID NOS: 29

<210> SEQ ID NO 1
<211> LENGTH: 4
<212> TYPE: PRT
<213> ORGANISM: Artificial Sequence
<220> FEATURE:
<223> OTHER INFORMATION: Peptide Domain

<400> SEQUENCE: 1

Asn Pro Ile Tyr
1

<210> SEQ ID NO 2
<211> LENGTH: 661
<212> TYPE: PRT
<213> ORGANISM: Mus musculus

<400> SEQUENCE: 2

Met Glu Leu Glu Val Pro Asp Glu Ala Glu Ser Ala Glu Ala Gly Ala
1               5                   10                  15
```

-continued

Val Thr Ala Glu Ala Ala Trp Ser Ala Glu Ser Gly Ala Ala Ala Gly
            20              25              30

Met Thr Gln Lys Lys Ala Gly Leu Ala Glu Ala Pro Leu Val Thr Gly
            35              40              45

Gln Pro Gly Pro Gly His Gly Lys Lys Leu Gly His Arg Gly Val Asp
 50              55              60

Ala Ser Gly Glu Thr Thr Tyr Lys Lys Thr Thr Ser Ser Thr Leu Lys
 65              70              75              80

Gly Ala Ile Gln Leu Gly Ile Gly Tyr Thr Val Gly Asn Leu Ser Ser
                85              90              95

Lys Pro Glu Arg Asp Val Leu Met Gln Asp Phe Tyr Val Met Glu Ser
            100             105             110

Ile Phe Phe Pro Ser Glu Gly Ser Asn Phe Thr Pro Ala His His Phe
        115             120             125

Gln Asp Phe Arg Phe Lys Thr Tyr Ala Pro Val Ala Phe Arg Tyr Phe
 130             135             140

Arg Glu Leu Phe Gly Ile Arg Pro Asp Asp Tyr Leu Tyr Ser Leu Cys
145             150             155             160

Asn Glu Pro Leu Ile Glu Leu Ser Asn Pro Gly Ala Ser Gly Ser Val
                165             170             175

Phe Tyr Val Thr Ser Asp Asp Glu Phe Ile Ile Lys Thr Val Met His
            180             185             190

Lys Glu Ala Glu Phe Leu Gln Lys Leu Leu Pro Gly Tyr Tyr Met Asn
        195             200             205

Leu Asn Gln Asn Pro Arg Thr Leu Leu Pro Lys Phe Tyr Gly Leu Tyr
    210             215             220

Cys Val Gln Ser Gly Gly Lys Asn Ile Arg Val Val Met Asn Asn
225             230             235             240

Val Leu Pro Arg Val Lys Met His Leu Lys Phe Asp Leu Lys Gly
                245             250             255

Ser Thr Tyr Lys Arg Arg Ala Ser Lys Lys Glu Lys Glu Lys Ser Leu
            260             265             270

Pro Thr Tyr Lys Asp Leu Asp Phe Met Gln Asp Met Pro Glu Gly Leu
        275             280             285

Leu Leu Asp Ser Asp Thr Phe Gly Ala Leu Val Lys Thr Leu Gln Arg
    290             295             300

Asp Cys Leu Val Leu Glu Ser Phe Lys Ile Met Asp Tyr Ser Leu Leu
305             310             315             320

Leu Gly Val His Asn Ile Asp Gln Gln Glu Arg Gln Ala Glu
                325             330             335

Gly Ala Gln Ser Lys Ala Asp Glu Lys Arg Pro Val Ala Gln Lys Ala
            340             345             350

Leu Tyr Ser Thr Ala Met Glu Ser Ile Gln Gly Gly Ala Ala Arg Gly
        355             360             365

Glu Ala Ile Glu Thr Asp Asp Thr Met Gly Gly Ile Pro Ala Val Asn
    370             375             380

Gly Arg Gly Glu Arg Leu Leu His Ile Gly Ile Asp Ile Leu
385             390             395             400

Gln Ser Tyr Arg Phe Ile Lys Lys Leu Glu His Thr Trp Lys Ala Leu
                405             410             415

Val His Asp Gly Asp Thr Val Ser Val His Arg Pro Ser Phe Tyr Ala
            420             425             430

Glu Arg Phe Phe Lys Phe Met Ser Ser Thr Val Phe Arg Lys Ser Ser

-continued

```
                435                 440                 445
Ser Leu Lys Ser Ser Pro Ser Lys Lys Gly Arg Gly Ala Leu Leu Ala
        450                 455                 460
Val Lys Pro Leu Gly Pro Thr Ala Ala Phe Ser Ala Ser Gln Ile Pro
465                 470                 475                 480
Ser Glu Arg Glu Asp Val Gln Tyr Asp Leu Arg Gly Ala Arg Ser Tyr
                485                 490                 495
Pro Thr Leu Glu Asp Glu Gly Arg Pro Asp Leu Leu Pro Cys Thr Pro
                    500                 505                 510
Pro Ser Phe Glu Glu Ala Thr Thr Ala Ser Ile Ala Thr Thr Leu Ser
            515                 520                 525
Ser Thr Ser Leu Ser Ile Pro Glu Arg Ser Pro Ser Asp Thr Ser Glu
    530                 535                 540
Gln Pro Arg Tyr Arg Arg Thr Gln Ser Ser Gly Gln Asp Gly Arg
545                 550                 555                 560
Pro Gln Glu Glu Pro His Ala Glu Asp Leu Gln Lys Ile Thr Val Gln
                565                 570                 575
Val Glu Pro Val Cys Gly Val Gly Val Pro Lys Glu Glu Gly Ala
                    580                 585                 590
Gly Val Glu Val Pro Pro Cys Gly Ala Ser Ala Ala Ser Val Glu
            595                 600                 605
Ile Asp Ala Ala Ser Gln Ala Ser Glu Pro Ala Ser Gln Ala Ser Asp
        610                 615                 620
Glu Glu Asp Ala Pro Ser Thr Asp Ile Tyr Phe Pro Thr Asp Glu Arg
625                 630                 635                 640
Ser Trp Val Tyr Ser Pro Leu His Tyr Ser Ala Arg Pro Ala Ser Asp
                645                 650                 655
Gly Glu Ser Asp Thr
                660

<210> SEQ ID NO 3
<211> LENGTH: 178
<212> TYPE: PRT
<213> ORGANISM: Mus musculus

<400> SEQUENCE: 3

Glu Asp Val Gln Tyr Asp Leu Arg Gly Ala Arg Ser Tyr Pro Thr Leu
1               5                   10                  15
Glu Asp Glu Gly Arg Pro Asp Leu Leu Pro Cys Thr Pro Pro Ser Phe
            20                  25                  30
Glu Glu Ala Thr Thr Ala Ser Ile Ala Thr Thr Leu Ser Ser Thr Ser
        35                  40                  45
Leu Ser Ile Pro Glu Arg Ser Pro Ser Asp Thr Ser Glu Gln Pro Arg
    50                  55                  60
Tyr Arg Arg Thr Gln Ser Ser Gly Gln Asp Gly Arg Pro Gln Glu
65                  70                  75                  80
Glu Pro His Ala Glu Asp Leu Gln Lys Ile Thr Val Gln Val Glu Pro
                85                  90                  95
Val Cys Gly Val Gly Val Pro Lys Glu Glu Gly Ala Gly Val Glu
            100                 105                 110
Val Pro Pro Cys Gly Ala Ser Ala Ala Ser Val Glu Ile Asp Ala
        115                 120                 125
Ala Ser Gln Ala Ser Glu Pro Ala Ser Gln Ala Ser Asp Glu Glu Asp
    130                 135                 140
```

```
Ala Pro Ser Thr Asp Ile Tyr Phe Pro Thr Asp Glu Arg Ser Trp Val
145                 150                 155                 160

Tyr Ser Pro Leu His Tyr Ser Ala Arg Pro Ala Ser Asp Gly Glu Ser
                165                 170                 175

Asp Thr

<210> SEQ ID NO 4
<211> LENGTH: 25
<212> TYPE: PRT
<213> ORGANISM: Mus musculus

<400> SEQUENCE: 4

Thr Asp Glu Arg Ser Trp Val Tyr Ser Pro Leu His Tyr Ser Ala Arg
1               5                   10                  15

Pro Ala Ser Asp Gly Ser Asp Thr
            20                  25

<210> SEQ ID NO 5
<211> LENGTH: 15
<212> TYPE: PRT
<213> ORGANISM: Mus musculus

<400> SEQUENCE: 5

Asp Glu Arg Ser Trp Val Tyr Ser Pro Leu His Tyr Ser Ala Arg
1               5                   10                  15

<210> SEQ ID NO 6
<211> LENGTH: 2540
<212> TYPE: PRT
<213> ORGANISM: Homo sapiens

<400> SEQUENCE: 6

Met Val Ala Leu Ser Leu Lys Ile Ser Ile Gly Asn Val Val Lys Thr
1               5                   10                  15

Met Gln Phe Glu Pro Ser Thr Met Val Tyr Asp Ala Cys Arg Ile Ile
                20                  25                  30

Arg Glu Arg Ile Pro Glu Ala Pro Ala Gly Pro Pro Ser Asp Phe Gly
            35                  40                  45

Leu Phe Leu Ser Asp Asp Asp Pro Lys Lys Gly Ile Trp Leu Glu Ala
    50                  55                  60

Gly Lys Ala Leu Asp Tyr Tyr Met Leu Arg Asn Gly Asp Thr Met Glu
65                  70                  75                  80

Tyr Arg Lys Lys Gln Arg Pro Leu Lys Ile Arg Met Leu Asp Gly Thr
                85                  90                  95

Val Lys Thr Ile Met Val Asp Asp Ser Lys Thr Val Thr Asp Met Leu
                100                 105                 110

Met Thr Ile Cys Ala Arg Ile Gly Ile Thr Asn His Asp Glu Tyr Ser
            115                 120                 125

Leu Val Arg Glu Leu Met Glu Glu Lys Lys Glu Glu Ile Thr Gly Thr
    130                 135                 140

Leu Arg Lys Asp Lys Thr Leu Leu Arg Asp Glu Lys Lys Met Glu Lys
145                 150                 155                 160

Leu Lys Gln Lys Leu His Thr Asp Asp Glu Leu Asn Trp Leu Asp His
                165                 170                 175

Gly Arg Thr Leu Arg Glu Gln Gly Val Glu Glu His Glu Thr Leu Leu
                180                 185                 190

Leu Arg Arg Lys Phe Phe Tyr Ser Asp Gln Asn Val Asp Ser Arg Asp
            195                 200                 205
```

```
-continued

Pro Val Gln Leu Asn Leu Leu Tyr Val Gln Ala Arg Asp Asp Ile Leu
210                 215                 220

Asn Gly Ser His Pro Val Ser Phe Asp Lys Ala Cys Glu Phe Ala Gly
225                 230                 235                 240

Phe Gln Cys Gln Ile Gln Phe Gly Pro His Asn Glu Gln Lys His Lys
                245                 250                 255

Ala Gly Phe Leu Asp Leu Lys Asp Phe Leu Pro Lys Glu Tyr Val Lys
            260                 265                 270

Gln Lys Gly Glu Arg Lys Ile Phe Gln Ala His Lys Asn Cys Gly Gln
        275                 280                 285

Met Ser Glu Ile Glu Ala Lys Val Arg Tyr Val Lys Leu Ala Arg Ser
290                 295                 300

Leu Lys Thr Tyr Gly Val Ser Phe Phe Leu Val Lys Glu Lys Met Lys
305                 310                 315                 320

Gly Lys Asn Lys Leu Val Pro Arg Leu Leu Gly Ile Thr Lys Glu Cys
                325                 330                 335

Val Met Arg Val Asp Glu Lys Thr Lys Glu Val Ile Gln Glu Trp Asn
            340                 345                 350

Leu Thr Asn Ile Lys Arg Trp Ala Ala Ser Pro Lys Ser Phe Thr Leu
        355                 360                 365

Asp Phe Gly Asp Tyr Gln Asp Gly Tyr Tyr Ser Val Gln Thr Thr Glu
370                 375                 380

Gly Glu Gln Ile Ala Gln Leu Ile Ala Gly Tyr Ile Asp Ile Ile Leu
385                 390                 395                 400

Lys Lys Lys Lys Ser Lys Asp His Phe Gly Leu Glu Gly Asp Glu Glu
                405                 410                 415

Ser Thr Met Leu Glu Asp Ser Val Ser Pro Lys Lys Ser Thr Val Leu
            420                 425                 430

Gln Gln Gln Tyr Asn Arg Val Gly Lys Val Glu His Gly Ser Val Ala
        435                 440                 445

Leu Pro Ala Ile Met Arg Ser Gly Ala Ser Gly Pro Glu Asn Phe Gln
450                 455                 460

Val Gly Ser Met Pro Pro Ala Gln Gln Gln Ile Thr Ser Gly Gln Met
465                 470                 475                 480

His Arg Gly His Met Pro Pro Leu Thr Ser Ala Gln Gln Ala Leu Thr
                485                 490                 495

Gly Thr Ile Asn Ser Ser Met Gln Ala Val Gln Ala Ala Gln Ala Thr
            500                 505                 510

Leu Asp Asp Phe Asp Thr Leu Pro Pro Leu Gly Gln Asp Ala Ala Ser
        515                 520                 525

Lys Ala Trp Arg Lys Asn Lys Met Asp Glu Ser Lys His Glu Ile His
530                 535                 540

Ser Gln Val Asp Ala Ile Thr Ala Gly Thr Ala Ser Val Val Asn Leu
545                 550                 555                 560

Thr Ala Gly Asp Pro Ala Glu Thr Asp Tyr Thr Ala Val Gly Cys Ala
                565                 570                 575

Val Thr Thr Ile Ser Ser Asn Leu Thr Glu Met Ser Arg Gly Val Lys
            580                 585                 590

Leu Leu Ala Ala Leu Leu Glu Asp Glu Gly Gly Ser Gly Arg Pro Leu
        595                 600                 605

Leu Gln Ala Ala Lys Gly Leu Ala Gly Ala Val Ser Glu Leu Leu Arg
610                 615                 620
```

```
                    -continued

Ser Ala Gln Pro Ala Ser Ala Glu Pro Arg Gln Asn Leu Leu Gln Ala
625                 630                 635                 640

Ala Gly Asn Val Gly Gln Ala Ser Gly Glu Leu Leu Gln Gln Ile Gly
                645                 650                 655

Glu Ser Asp Thr Asp Pro His Phe Gln Asp Ala Leu Met Gln Leu Ala
            660                 665                 670

Lys Ala Val Ala Ser Ala Ala Ala Leu Val Leu Lys Ala Lys Ser
        675                 680                 685

Val Ala Gln Arg Thr Glu Asp Ser Gly Leu Gln Thr Gln Val Ile Ala
    690                 695                 700

Ala Ala Thr Gln Cys Ala Leu Ser Thr Ser Gln Leu Val Ala Cys Thr
705                 710                 715                 720

Lys Val Val Ala Pro Thr Ile Ser Ser Pro Val Cys Gln Glu Gln Leu
                725                 730                 735

Val Glu Ala Gly Arg Leu Val Ala Lys Ala Val Glu Gly Cys Val Ser
            740                 745                 750

Ala Ser Gln Ala Ala Thr Glu Asp Gly Gln Leu Leu Arg Gly Val Gly
        755                 760                 765

Ala Ala Ala Thr Ala Val Thr Gln Ala Leu Asn Glu Leu Leu Gln His
    770                 775                 780

Val Lys Ala His Ala Thr Gly Ala Gly Pro Ala Gly Arg Tyr Asp Gln
785                 790                 795                 800

Ala Thr Asp Thr Ile Leu Thr Val Thr Glu Asn Ile Phe Ser Ser Met
                805                 810                 815

Gly Asp Ala Gly Glu Met Val Gly Gln Ala Arg Ile Leu Ala Gln Ala
            820                 825                 830

Thr Ser Asp Leu Val Asn Ala Ile Lys Ala Asp Ala Glu Gly Glu Ser
        835                 840                 845

Asp Leu Glu Asn Ser Arg Lys Leu Leu Ser Ala Lys Ile Leu Ala
    850                 855                 860

Asp Ala Thr Ala Lys Met Val Glu Ala Ala Lys Gly Ala Ala Ala His
865                 870                 875                 880

Pro Asp Ser Glu Glu Gln Gln Gln Arg Leu Arg Glu Ala Ala Glu Gly
                885                 890                 895

Leu Arg Met Ala Thr Asn Ala Ala Ala Gln Asn Ala Ile Lys Lys Lys
            900                 905                 910

Leu Val Gln Arg Leu Glu His Ala Ala Lys Gln Ala Ala Ala Ser Ala
        915                 920                 925

Thr Gln Thr Ile Ala Ala Ala Gln His Ala Ala Ser Thr Pro Lys Ala
    930                 935                 940

Ser Ala Gly Pro Gln Pro Leu Leu Val Gln Ser Cys Lys Ala Val Ala
945                 950                 955                 960

Glu Gln Ile Pro Leu Leu Val Gln Gly Val Arg Gly Ser Gln Ala Gln
                965                 970                 975

Pro Asp Ser Pro Ser Ala Gln Leu Ala Leu Ile Ala Ala Ser Gln Ser
            980                 985                 990

Phe Leu Gln Pro Gly Gly Lys Met Val Ala Ala Lys Ala Ser Val
        995                 1000                1005

Pro Thr Ile Gln Asp Gln Ala Ser Ala Met Gln Leu Ser Gln Cys
    1010                1015                1020

Ala Lys Asn Leu Gly Thr Ala Leu Ala Glu Leu Arg Thr Ala Ala
    1025                1030                1035

Gln Lys Ala Gln Glu Ala Cys Gly Pro Leu Glu Met Asp Ser Ala
```

-continued

```
            1040                1045                1050
Leu Ser Val Val Gln Asn Leu Glu Lys Asp Leu Gln Glu Val Lys
        1055                1060                1065
Ala Ala Ala Arg Asp Gly Lys Leu Lys Pro Leu Pro Gly Glu Thr
        1070                1075                1080
Met Glu Lys Cys Thr Gln Asp Leu Gly Asn Ser Thr Lys Ala Val
        1085                1090                1095
Ser Ser Ala Ile Ala Gln Leu Leu Gly Glu Val Ala Gln Gly Asn
        1100                1105                1110
Glu Asn Tyr Ala Gly Ile Ala Ala Arg Asp Val Ala Gly Gly Leu
        1115                1120                1125
Arg Ser Leu Ala Gln Ala Ala Arg Gly Val Ala Ala Leu Thr Ser
        1130                1135                1140
Asp Pro Ala Val Gln Ala Ile Val Leu Asp Thr Ala Ser Asp Val
        1145                1150                1155
Leu Asp Lys Ala Ser Ser Leu Ile Glu Glu Ala Lys Lys Ala Ala
        1160                1165                1170
Gly His Pro Gly Asp Pro Glu Ser Gln Gln Arg Leu Ala Gln Val
        1175                1180                1185
Ala Lys Ala Val Thr Gln Ala Leu Asn Arg Cys Val Ser Cys Leu
        1190                1195                1200
Pro Gly Gln Arg Asp Val Asp Asn Ala Leu Arg Ala Val Gly Asp
        1205                1210                1215
Ala Ser Lys Arg Leu Leu Ser Asp Ser Leu Pro Pro Ser Thr Gly
        1220                1225                1230
Thr Phe Gln Glu Ala Gln Ser Arg Leu Asn Glu Ala Ala Ala Gly
        1235                1240                1245
Leu Asn Gln Ala Ala Thr Glu Leu Val Gln Ala Ser Arg Gly Thr
        1250                1255                1260
Pro Gln Asp Leu Ala Arg Ala Ser Gly Arg Phe Gly Gln Asp Phe
        1265                1270                1275
Ser Thr Phe Leu Glu Ala Gly Val Glu Met Ala Gly Gln Ala Pro
        1280                1285                1290
Ser Gln Glu Asp Arg Ala Gln Val Val Ser Asn Leu Lys Gly Ile
        1295                1300                1305
Ser Met Ser Ser Ser Lys Leu Leu Leu Ala Ala Lys Ala Leu Ser
        1310                1315                1320
Thr Asp Pro Ala Ala Pro Asn Leu Lys Ser Gln Leu Ala Ala Ala
        1325                1330                1335
Ala Arg Ala Val Thr Asp Ser Ile Asn Gln Leu Ile Thr Met Cys
        1340                1345                1350
Thr Gln Gln Ala Pro Gly Gln Lys Glu Cys Asp Asn Ala Leu Arg
        1355                1360                1365
Glu Leu Glu Thr Val Arg Glu Leu Leu Glu Asn Pro Val Gln Pro
        1370                1375                1380
Ile Asn Asp Met Ser Tyr Phe Gly Cys Leu Asp Ser Val Met Glu
        1385                1390                1395
Asn Ser Lys Val Leu Gly Glu Ala Met Thr Gly Ile Ser Gln Asn
        1400                1405                1410
Ala Lys Asn Gly Asn Leu Pro Glu Phe Gly Asp Ala Ile Ser Thr
        1415                1420                1425
Ala Ser Lys Ala Leu Cys Gly Phe Thr Glu Ala Ala Ala Gln Ala
        1430                1435                1440
```

-continued

```
Ala Tyr Leu Val Gly Val Ser Asp Pro Asn Ser Gln Ala Gly Gln
    1445                1450                1455

Gln Gly Leu Val Glu Pro Thr Gln Phe Ala Arg Ala Asn Gln Ala
    1460                1465                1470

Ile Gln Met Ala Cys Gln Ser Leu Gly Glu Pro Gly Cys Thr Gln
    1475                1480                1485

Ala Gln Val Leu Ser Ala Ala Thr Ile Val Ala Lys His Thr Ser
    1490                1495                1500

Ala Leu Cys Asn Ser Cys Arg Leu Ala Ser Ala Arg Thr Thr Asn
    1505                1510                1515

Pro Thr Ala Lys Arg Gln Phe Val Gln Ser Ala Lys Glu Val Ala
    1520                1525                1530

Asn Ser Thr Ala Asn Leu Val Lys Thr Ile Lys Ala Leu Asp Gly
    1535                1540                1545

Ala Phe Thr Glu Glu Asn Arg Ala Gln Cys Arg Ala Ala Thr Ala
    1550                1555                1560

Pro Leu Leu Glu Ala Val Asp Asn Leu Ser Ala Phe Ala Ser Asn
    1565                1570                1575

Pro Glu Phe Ser Ser Ile Pro Ala Gln Ile Ser Pro Glu Gly Arg
    1580                1585                1590

Ala Ala Met Glu Pro Ile Val Ile Ser Ala Lys Thr Met Leu Glu
    1595                1600                1605

Ser Ala Gly Gly Leu Ile Gln Thr Ala Arg Ala Leu Ala Val Asn
    1610                1615                1620

Pro Arg Asp Pro Pro Ser Trp Ser Val Leu Ala Gly His Ser Arg
    1625                1630                1635

Thr Val Ser Asp Ser Ile Lys Lys Leu Ile Thr Ser Met Arg Asp
    1640                1645                1650

Lys Ala Pro Gly Gln Leu Glu Cys Glu Thr Ala Ile Ala Ala Leu
    1655                1660                1665

Asn Ser Cys Leu Arg Asp Leu Asp Gln Ala Ser Leu Ala Ala Val
    1670                1675                1680

Ser Gln Gln Leu Ala Pro Arg Glu Gly Ile Ser Gln Glu Ala Leu
    1685                1690                1695

His Thr Gln Met Leu Thr Ala Val Gln Glu Ile Ser His Leu Ile
    1700                1705                1710

Glu Pro Leu Ala Asn Ala Ala Arg Ala Glu Ala Ser Gln Leu Gly
    1715                1720                1725

His Lys Val Ser Gln Met Ala Gln Tyr Phe Glu Pro Leu Thr Leu
    1730                1735                1740

Ala Ala Val Gly Ala Ala Ser Lys Thr Leu Ser His Pro Gln Gln
    1745                1750                1755

Met Ala Leu Leu Asp Gln Thr Lys Thr Leu Ala Glu Ser Ala Leu
    1760                1765                1770

Gln Leu Leu Tyr Thr Ala Lys Glu Ala Gly Gly Asn Pro Lys Gln
    1775                1780                1785

Ala Ala His Thr Gln Glu Ala Leu Glu Glu Ala Val Gln Met Met
    1790                1795                1800

Thr Glu Ala Val Glu Asp Leu Thr Thr Thr Leu Asn Glu Ala Ala
    1805                1810                1815

Ser Ala Ala Gly Val Val Gly Gly Met Val Asp Ser Ile Thr Gln
    1820                1825                1830
```

-continued

Ala Ile Asn Gln Leu Asp Glu Gly Pro Met Gly Glu Pro Glu Gly
    1835                1840                1845

Ser Phe Val Asp Tyr Gln Thr Thr Met Val Arg Thr Ala Lys Ala
    1850                1855                1860

Ile Ala Val Thr Val Gln Glu Met Val Thr Lys Ser Asn Thr Ser
    1865                1870                1875

Pro Glu Glu Leu Gly Pro Leu Ala Asn Gln Leu Thr Ser Asp Tyr
    1880                1885                1890

Gly Arg Leu Ala Ser Glu Ala Lys Pro Ala Ala Val Ala Ala Glu
    1895                1900                1905

Asn Glu Glu Ile Gly Ser His Ile Lys His Arg Val Gln Glu Leu
    1910                1915                1920

Gly His Gly Cys Ala Ala Leu Val Thr Lys Ala Gly Ala Leu Gln
    1925                1930                1935

Cys Ser Pro Ser Asp Ala Tyr Thr Lys Lys Glu Leu Ile Glu Cys
    1940                1945                1950

Ala Arg Arg Val Ser Glu Lys Val Ser His Val Leu Ala Ala Leu
    1955                1960                1965

Gln Ala Gly Asn Arg Gly Thr Gln Ala Cys Ile Thr Ala Ala Ser
    1970                1975                1980

Ala Val Ser Gly Ile Ile Ala Asp Leu Asp Thr Thr Ile Met Phe
    1985                1990                1995

Ala Thr Ala Gly Thr Leu Asn Arg Glu Gly Thr Glu Thr Phe Ala
    2000                2005                2010

Asp His Arg Glu Gly Ile Leu Lys Thr Ala Lys Val Leu Val Glu
    2015                2020                2025

Asp Thr Lys Val Leu Val Gln Asn Ala Ala Gly Ser Gln Glu Lys
    2030                2035                2040

Leu Ala Gln Ala Ala Gln Ser Ser Val Ala Thr Ile Thr Arg Leu
    2045                2050                2055

Ala Asp Val Val Lys Leu Gly Ala Ala Ser Leu Gly Ala Glu Asp
    2060                2065                2070

Pro Glu Thr Gln Val Val Leu Ile Asn Ala Val Lys Asp Val Ala
    2075                2080                2085

Lys Ala Leu Gly Asp Leu Ile Ser Ala Thr Lys Ala Ala Ala Gly
    2090                2095                2100

Lys Val Gly Asp Asp Pro Ala Val Trp Gln Leu Lys Asn Ser Ala
    2105                2110                2115

Lys Val Met Val Thr Asn Val Thr Ser Leu Leu Lys Thr Val Lys
    2120                2125                2130

Ala Val Glu Asp Glu Ala Thr Lys Gly Thr Arg Ala Leu Glu Ala
    2135                2140                2145

Thr Thr Glu His Ile Arg Gln Glu Leu Ala Val Phe Cys Ser Pro
    2150                2155                2160

Glu Pro Pro Ala Lys Thr Ser Thr Pro Glu Asp Phe Ile Arg Met
    2165                2170                2175

Thr Lys Gly Ile Thr Met Ala Thr Ala Lys Ala Val Ala Ala Gly
    2180                2185                2190

Asn Ser Cys Arg Gln Glu Asp Val Ile Ala Thr Ala Asn Leu Ser
    2195                2200                2205

Arg Arg Ala Ile Ala Asp Met Leu Arg Ala Cys Lys Glu Ala Ala
    2210                2215                2220

Tyr His Pro Glu Val Ala Pro Asp Val Arg Leu Arg Ala Leu His

-continued

```
                2225                2230                2235
    Tyr Gly Arg Glu Cys Ala Asn Gly Tyr Leu Glu Leu Leu Asp His
        2240                2245                2250

Val Leu Leu Thr Leu Gln Lys Pro Ser Pro Glu Leu Lys Gln Gln
        2255                2260                2265

Leu Thr Gly His Ser Lys Arg Val Ala Gly Ser Val Thr Glu Leu
        2270                2275                2280

Ile Gln Ala Ala Glu Ala Met Lys Gly Thr Glu Trp Val Asp Pro
        2285                2290                2295

Glu Asp Pro Thr Val Ile Ala Glu Asn Glu Leu Leu Gly Ala Ala
        2300                2305                2310

Ala Ala Ile Glu Ala Ala Lys Lys Leu Glu Gln Leu Lys Pro
        2315                2320                2325

Arg Ala Lys Pro Lys Glu Ala Asp Glu Ser Leu Asn Phe Glu Glu
        2330                2335                2340

Gln Ile Leu Glu Ala Ala Lys Ser Ile Ala Ala Ala Thr Ser Ala
        2345                2350                2355

Leu Val Lys Ala Ala Ser Ala Ala Gln Arg Glu Leu Val Ala Gln
        2360                2365                2370

Gly Lys Val Gly Ala Ile Pro Ala Asn Ala Leu Asp Asp Gly Gln
        2375                2380                2385

Trp Ser Gln Gly Leu Ile Ser Ala Ala Arg Met Val Ala Ala Ala
        2390                2395                2400

Thr Asn Asn Leu Cys Glu Ala Ala Asn Ala Ala Val Gln Gly His
        2405                2410                2415

Ala Ser Gln Glu Lys Leu Ile Ser Ser Ala Lys Gln Val Ala Ala
        2420                2425                2430

Ser Thr Ala Gln Leu Leu Val Ala Cys Lys Val Lys Ala Asp Gln
        2435                2440                2445

Asp Ser Glu Ala Met Arg Leu Gln Ala Ala Gly Asn Ala Val Lys
        2450                2455                2460

Arg Ala Ser Asp Asn Leu Val Lys Ala Ala Gln Lys Ala Ala Ala
        2465                2470                2475

Phe Glu Glu Gln Glu Asn Glu Thr Val Val Lys Glu Lys Met
        2480                2485                2490

Val Gly Gly Ile Ala Gln Ile Ile Ala Ala Gln Glu Glu Met Leu
        2495                2500                2505

Arg Lys Glu Arg Glu Leu Glu Glu Ala Arg Lys Lys Leu Ala Gln
        2510                2515                2520

Ile Arg Gln Gln Gln Tyr Lys Phe Leu Pro Ser Glu Leu Arg Asp
        2525                2530                2535

Glu His
        2540

<210> SEQ ID NO 7
<211> LENGTH: 450
<212> TYPE: PRT
<213> ORGANISM: Homo sapiens

<400> SEQUENCE: 7

Met Val Ala Leu Ser Leu Lys Ile Ser Ile Gly Asn Val Val Lys Thr
  1               5                  10                 15

Met Gln Phe Glu Pro Ser Thr Met Val Tyr Asp Ala Cys Arg Ile Ile
            20                  25                  30
```

-continued

```
Arg Glu Arg Ile Pro Glu Ala Pro Gly Pro Pro Ser Asp Phe Gly
         35                  40                  45

Leu Phe Leu Ser Asp Asp Pro Lys Lys Gly Ile Trp Leu Glu Ala
 50                  55                  60

Gly Lys Ala Leu Asp Tyr Tyr Met Leu Arg Asn Gly Asp Thr Met Glu
 65                  70                  75                  80

Tyr Arg Lys Lys Gln Arg Pro Leu Lys Ile Arg Met Leu Asp Gly Thr
                 85                  90                  95

Val Lys Thr Ile Met Val Asp Asp Ser Lys Thr Val Thr Asp Met Leu
                100                 105                 110

Met Thr Ile Cys Ala Arg Ile Gly Ile Thr Asn His Asp Glu Tyr Ser
             115                 120                 125

Leu Val Arg Glu Leu Met Glu Glu Lys Glu Glu Ile Thr Gly Thr
130                 135                 140

Leu Arg Lys Asp Lys Thr Leu Leu Arg Asp Glu Lys Lys Met Glu Lys
145                 150                 155                 160

Leu Lys Gln Lys Leu His Thr Asp Asp Glu Leu Asn Trp Leu Asp His
                165                 170                 175

Gly Arg Thr Leu Arg Glu Gln Gly Val Glu Glu His Glu Thr Leu Leu
             180                 185                 190

Leu Arg Arg Lys Phe Phe Tyr Ser Asp Gln Asn Val Asp Ser Arg Asp
             195                 200                 205

Pro Val Gln Leu Asn Leu Leu Tyr Val Gln Ala Arg Asp Asp Ile Leu
         210                 215                 220

Asn Gly Ser His Pro Val Ser Phe Asp Lys Ala Cys Glu Phe Ala Gly
225                 230                 235                 240

Phe Gln Cys Gln Ile Gln Phe Gly Pro His Asn Glu Gln Lys His Lys
                245                 250                 255

Ala Gly Phe Leu Asp Leu Lys Asp Phe Leu Pro Lys Glu Tyr Val Lys
             260                 265                 270

Gln Lys Gly Glu Arg Lys Ile Phe Gln Ala His Lys Asn Cys Gly Gln
         275                 280                 285

Met Ser Glu Ile Glu Ala Lys Val Arg Tyr Val Lys Leu Ala Arg Ser
290                 295                 300

Leu Lys Thr Tyr Gly Val Ser Phe Phe Leu Val Lys Glu Lys Met Lys
305                 310                 315                 320

Gly Lys Asn Lys Leu Val Pro Arg Leu Leu Gly Ile Thr Lys Glu Cys
                325                 330                 335

Val Met Arg Val Asp Glu Lys Thr Lys Glu Val Ile Gln Glu Trp Asn
             340                 345                 350

Leu Thr Asn Ile Lys Arg Trp Ala Ala Ser Pro Lys Ser Phe Thr Leu
         355                 360                 365

Asp Phe Gly Asp Tyr Gln Asp Gly Tyr Tyr Ser Val Gln Thr Thr Glu
     370                 375                 380

Gly Glu Gln Ile Ala Gln Leu Ile Ala Gly Tyr Ile Asp Ile Ile Leu
385                 390                 395                 400

Lys Lys Lys Lys Ser Lys Asp His Phe Gly Leu Glu Gly Asp Glu Glu
                405                 410                 415

Ser Thr Met Leu Glu Asp Ser Val Ser Pro Lys Lys Ser Thr Val Leu
             420                 425                 430

Gln Gln Gln Tyr Asn Arg Val Gly Lys Val Glu His Gly Ser Val Ala
         435                 440                 445

Leu Pro
```

450

<210> SEQ ID NO 8
<211> LENGTH: 300
<212> TYPE: PRT
<213> ORGANISM: Homo sapiens

<400> SEQUENCE: 8

Leu Leu Arg Asp Glu Lys Lys Met Glu Lys Leu Lys Gln Lys Leu His
1               5                   10                  15

Thr Asp Asp Glu Leu Asn Trp Leu Asp His Gly Arg Thr Leu Arg Glu
            20                  25                  30

Gln Gly Val Glu Glu His Glu Thr Leu Leu Arg Arg Lys Phe Phe
        35                  40                  45

Tyr Ser Asp Gln Asn Val Ser Arg Asp Pro Val Gln Leu Asn Leu
    50                  55                  60

Leu Tyr Val Gln Ala Arg Asp Ile Leu Asn Gly Ser His Pro Val
65                  70                  75                  80

Ser Phe Asp Lys Ala Cys Glu Phe Ala Gly Phe Gln Cys Gln Ile Gln
                85                  90                  95

Phe Gly Pro His Asn Glu Gln Lys His Lys Ala Gly Phe Leu Asp Leu
            100                 105                 110

Lys Asp Phe Leu Pro Lys Glu Tyr Val Lys Gln Lys Gly Glu Arg Lys
        115                 120                 125

Ile Phe Gln Ala His Lys Asn Cys Gly Gln Met Ser Glu Ile Glu Ala
    130                 135                 140

Lys Val Arg Tyr Val Lys Leu Ala Arg Ser Leu Lys Thr Tyr Gly Val
145                 150                 155                 160

Ser Phe Phe Leu Val Lys Glu Lys Met Lys Gly Lys Asn Lys Leu Val
                165                 170                 175

Pro Arg Leu Leu Gly Ile Thr Lys Glu Cys Val Met Arg Val Asp Glu
            180                 185                 190

Lys Thr Lys Glu Val Ile Gln Glu Trp Asn Leu Thr Asn Ile Lys Arg
        195                 200                 205

Trp Ala Ala Ser Pro Lys Ser Phe Thr Leu Asp Phe Gly Asp Tyr Gln
    210                 215                 220

Asp Gly Tyr Tyr Ser Val Gln Thr Thr Glu Gly Glu Gln Ile Ala Gln
225                 230                 235                 240

Leu Ile Ala Gly Tyr Ile Asp Ile Ile Leu Lys Lys Lys Ser Lys
                245                 250                 255

Asp His Phe Gly Leu Glu Gly Asp Glu Glu Ser Thr Met Leu Glu Asp
            260                 265                 270

Ser Val Ser Pro Lys Lys Ser Thr Val Leu Gln Gln Tyr Asn Arg
        275                 280                 285

Val Gly Lys Val Glu His Gly Ser Val Ala Leu Pro
    290                 295                 300

<210> SEQ ID NO 9
<211> LENGTH: 229
<212> TYPE: PRT
<213> ORGANISM: Homo sapiens

<400> SEQUENCE: 9

Ser Arg Asp Pro Val Gln Leu Asn Leu Leu Tyr Val Gln Ala Arg Asp
1               5                   10                  15

Asp Ile Leu Asn Gly Ser His Pro Val Ser Phe Asp Lys Ala Cys Glu

-continued

```
                20                  25                  30
Phe Ala Gly Phe Gln Cys Gln Ile Gln Phe Gly Pro His Asn Glu Gln
         35                  40                  45
Lys His Lys Ala Gly Phe Leu Asp Leu Lys Asp Phe Leu Pro Lys Glu
 50                  55                  60
Tyr Val Lys Gln Lys Gly Glu Arg Lys Ile Phe Gln Ala His Lys Asn
 65                  70                  75                  80
Cys Gly Gln Met Ser Glu Ile Glu Ala Lys Val Arg Tyr Val Lys Leu
                 85                  90                  95
Ala Arg Ser Leu Lys Thr Tyr Gly Val Ser Phe Phe Leu Val Lys Glu
            100                 105                 110
Lys Met Lys Gly Lys Asn Lys Leu Val Pro Arg Leu Leu Gly Ile Thr
            115                 120                 125
Lys Glu Cys Val Met Arg Val Asp Glu Lys Thr Lys Glu Val Ile Gln
            130                 135                 140
Glu Trp Asn Leu Thr Asn Ile Lys Arg Trp Ala Ala Ser Pro Lys Ser
145                 150                 155                 160
Phe Thr Leu Asp Phe Gly Asp Tyr Gln Asp Gly Tyr Tyr Ser Val Gln
                165                 170                 175
Thr Thr Glu Gly Glu Gln Ile Ala Gln Leu Ile Ala Gly Tyr Ile Asp
            180                 185                 190
Ile Ile Leu Lys Lys Lys Ser Lys Asp His Phe Gly Leu Glu Gly
            195                 200                 205
Asp Glu Glu Ser Thr Met Leu Glu Asp Ser Val Ser Pro Lys Lys Ser
        210                 215                 220
Thr Val Leu Gln Gln
225

<210> SEQ ID NO 10
<211> LENGTH: 450
<212> TYPE: PRT
<213> ORGANISM: Mus musculus

<400> SEQUENCE: 10

Met Ser Ala Ile Gln Ala Ala Trp Pro Ser Gly Thr Glu Cys Ile Ala
 1               5                  10                  15
Lys Tyr Asn Phe His Gly Thr Ala Glu Gln Asp Leu Pro Phe Cys Lys
                20                  25                  30
Gly Asp Val Leu Thr Ile Val Ala Val Thr Lys Asp Pro Asn Trp Tyr
            35                  40                  45
Lys Ala Lys Asn Lys Val Gly Arg Glu Gly Ile Ile Pro Ala Asn Tyr
 50                  55                  60
Val Gln Lys Arg Glu Gly Val Lys Ala Gly Thr Lys Leu Ser Leu Met
 65                  70                  75                  80
Pro Trp Phe His Gly Lys Ile Thr Arg Glu Gln Ala Glu Arg Leu Leu
                 85                  90                  95
Tyr Pro Pro Glu Thr Gly Leu Phe Leu Val Arg Glu Ser Thr Asn Tyr
            100                 105                 110
Pro Gly Asp Tyr Thr Leu Cys Val Ser Cys Glu Gly Lys Val Glu His
            115                 120                 125
Tyr Arg Ile Met Tyr His Ala Ser Lys Leu Ser Ile Asp Glu Glu Val
            130                 135                 140
Tyr Phe Glu Asn Leu Met Gln Leu Val Glu His Tyr Thr Thr Asp Ala
145                 150                 155                 160
```

```
Asp Gly Leu Cys Thr Arg Leu Ile Lys Pro Lys Val Met Glu Gly Thr
                165                 170                 175

Val Ala Ala Gln Asp Glu Phe Tyr Arg Ser Gly Trp Ala Leu Asn Met
            180                 185                 190

Lys Glu Leu Lys Leu Leu Gln Thr Ile Gly Lys Gly Glu Phe Gly Asp
        195                 200                 205

Val Met Leu Gly Asp Tyr Arg Gly Asn Lys Val Ala Val Lys Cys Ile
    210                 215                 220

Lys Asn Asp Ala Thr Ala Gln Ala Phe Leu Ala Glu Ala Ser Val Met
225                 230                 235                 240

Thr Gln Leu Arg His Ser Asn Leu Val Gln Leu Leu Gly Val Ile Val
                245                 250                 255

Glu Glu Lys Gly Gly Leu Tyr Ile Val Thr Glu Tyr Met Ala Lys Gly
            260                 265                 270

Ser Leu Val Asp Tyr Leu Arg Ser Arg Gly Arg Ser Val Leu Gly Gly
        275                 280                 285

Asp Cys Leu Leu Lys Phe Ser Leu Asp Val Cys Glu Ala Met Glu Tyr
    290                 295                 300

Leu Glu Gly Asn Asn Phe Val His Arg Asp Leu Ala Ala Arg Asn Val
305                 310                 315                 320

Leu Val Ser Glu Asp Asn Val Ala Lys Val Ser Asp Phe Gly Leu Thr
                325                 330                 335

Lys Glu Ala Ser Ser Thr Gln Asp Thr Gly Lys Leu Pro Val Lys Trp
            340                 345                 350

Thr Ala Pro Glu Ala Leu Arg Glu Lys Lys Phe Ser Thr Lys Ser Asp
        355                 360                 365

Val Trp Ser Phe Gly Ile Leu Leu Trp Glu Ile Tyr Ser Phe Gly Arg
    370                 375                 380

Val Pro Tyr Pro Arg Ile Pro Leu Lys Asp Val Val Pro Arg Val Glu
385                 390                 395                 400

Lys Gly Tyr Lys Met Asp Ala Pro Asp Gly Cys Pro Pro Ala Val Tyr
                405                 410                 415

Glu Val Met Lys Asn Cys Trp His Leu Asp Ala Ala Thr Arg Pro Thr
            420                 425                 430

Phe Leu Gln Leu Arg Glu Gln Leu Glu His Ile Lys Thr His Glu Leu
        435                 440                 445

His Leu
    450

<210> SEQ ID NO 11
<211> LENGTH: 1090
<212> TYPE: PRT
<213> ORGANISM: Mus musculus

<400> SEQUENCE: 11

Met Ala Ala Ala Tyr Leu Asp Pro Asn Leu Asn His Thr Pro Ser Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His His Phe Glu Ser Ser Ser Glu
        35                  40                  45

Pro Thr Thr Trp Ala Ser Ile Ile Arg His Gly Asp Ala Thr Asp Val
    50                  55                  60

Arg Gly Ile Ile Gln Lys Ile Val Asp Ser His Lys Val Lys His Val
65                  70                  75                  80
```

```
Ala Cys Tyr Gly Phe Arg Leu Ser His Leu Arg Ser Glu Val His
                85                  90                  95

Trp Leu His Val Asp Met Gly Val Ser Ser Val Arg Glu Lys Tyr Glu
            100                 105                 110

Leu Ala His Pro Pro Glu Glu Trp Lys Tyr Glu Leu Arg Ile Arg Tyr
        115                 120                 125

Leu Pro Lys Gly Phe Leu Asn Gln Phe Thr Glu Asp Lys Pro Thr Leu
    130                 135                 140

Asn Phe Phe Tyr Gln Gln Val Lys Ser Asp Tyr Met Gln Glu Ile Ala
145                 150                 155                 160

Asp Gln Val Asp Gln Glu Ile Ala Leu Lys Leu Gly Cys Leu Glu Ile
                165                 170                 175

Arg Arg Ser Tyr Trp Glu Met Arg Gly Asn Ala Leu Glu Lys Lys Ser
            180                 185                 190

Asn Tyr Glu Val Leu Glu Lys Asp Val Gly Leu Lys Arg Phe Phe Pro
        195                 200                 205

Lys Ser Leu Leu Asp Ser Val Lys Ala Lys Thr Leu Arg Lys Leu Ile
    210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
            260                 265                 270

Ala Ile Gly Pro Glu Glu Gly Ile Ser Tyr Leu Thr Asp Lys Gly Cys
        275                 280                 285

Asn Pro Thr His Leu Ala Asp Phe Asn Gln Val Gln Thr Ile Gln Tyr
    290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
                325                 330                 335

Ala Glu Asn Met Ala Asp Leu Ile Asp Gly Tyr Cys Arg Leu Val Asn
            340                 345                 350

Gly Ala Thr Gln Ser Phe Ile Ile Arg Pro Gln Lys Glu Gly Glu Arg
        355                 360                 365

Ala Leu Pro Ser Ile Pro Lys Leu Ala Asn Ser Glu Lys Gln Gly Met
    370                 375                 380

Arg Thr His Ala Val Ser Val Ser His Cys Gln His Lys Val Lys Lys
385                 390                 395                 400

Ala Arg Arg Phe Leu Pro Leu Val Phe Cys Ser Leu Glu Pro Pro Pro
                405                 410                 415

Thr Asp Glu Ile Ser Gly Asp Glu Thr Asp Asp Tyr Ala Glu Ile Ile
            420                 425                 430

Asp Glu Glu Asp Thr Tyr Thr Met Pro Ser Lys Ser Tyr Gly Ile Asp
        435                 440                 445

Glu Ala Arg Asp Tyr Glu Ile Gln Arg Glu Arg Ile Glu Leu Gly Arg
    450                 455                 460

Cys Ile Gly Glu Gly Gln Phe Gly Asp Val His Gln Gly Val Tyr Leu
465                 470                 475                 480

Ser Pro Glu Asn Pro Ala Leu Ala Val Ala Ile Lys Thr Cys Lys Asn
                485                 490                 495
```

-continued

```
Cys Thr Ser Asp Ser Val Arg Glu Lys Phe Leu Gln Glu Ala Leu Thr
            500                 505                 510
Met Arg Gln Phe Asp His Pro His Ile Val Lys Leu Ile Gly Val Ile
        515                 520                 525
Thr Glu Asn Pro Val Trp Ile Ile Met Glu Leu Cys Thr Leu Gly Glu
    530                 535                 540
Leu Arg Ser Phe Leu Gln Val Arg Lys Tyr Ser Leu Asp Leu Ala Ser
545                 550                 555                 560
Leu Ile Leu Tyr Ala Tyr Gln Leu Ser Thr Ala Leu Ala Tyr Leu Glu
                565                 570                 575
Ser Lys Arg Phe Val His Arg Asp Ile Ala Ala Arg Asn Val Leu Val
            580                 585                 590
Ser Ser Asn Asp Cys Val Lys Leu Gly Asp Phe Gly Leu Ser Arg Tyr
        595                 600                 605
Met Glu Asp Ser Thr Tyr Tyr Lys Ala Ser Lys Gly Lys Leu Pro Ile
    610                 615                 620
Lys Trp Met Ala Pro Glu Ser Ile Asn Phe Arg Arg Phe Thr Ser Ala
625                 630                 635                 640
Ser Asp Val Trp Met Phe Gly Val Cys Met Trp Glu Ile Leu Met His
                645                 650                 655
Gly Val Lys Pro Phe Gln Gly Val Lys Asn Asn Asp Val Ile Gly Arg
            660                 665                 670
Ile Glu Asn Gly Glu Arg Leu Pro Met Pro Pro Asn Cys Pro Pro Thr
        675                 680                 685
Leu Tyr Ser Leu Met Thr Lys Cys Trp Ala Tyr Asp Pro Ser Arg Arg
    690                 695                 700
Pro Arg Phe Thr Glu Leu Lys Ala Gln Leu Ser Thr Ile Leu Glu Glu
705                 710                 715                 720
Glu Lys Val Gln Gln Glu Glu Arg Met Arg Met Glu Ser Arg Arg Gln
                725                 730                 735
Ala Thr Val Ser Trp Asp Ser Gly Gly Ser Asp Glu Ala Pro Pro Lys
            740                 745                 750
Pro Ser Arg Pro Gly Tyr Pro Ser Pro Arg Ser Ser Glu Gly Phe Tyr
        755                 760                 765
Pro Ser Pro Gln His Met Val Gln Thr Asn His Tyr Gln Val Ser Gly
    770                 775                 780
Tyr Pro Gly Ser His Gly Ile Pro Ala Met Ala Gly Ser Ile Tyr Gln
785                 790                 795                 800
Gly Gln Ala Ser Leu Leu Asp Gln Thr Glu Leu Trp Asn His Arg Pro
                805                 810                 815
Gln Glu Met Ser Met Trp Gln Pro Ser Val Glu Asp Ser Ala Ala Leu
            820                 825                 830
Asp Leu Arg Gly Met Gly Gln Val Leu Pro Pro His Leu Met Glu Glu
        835                 840                 845
Arg Leu Ile Arg Gln Gln Gln Glu Met Glu Glu Asp Gln Arg Trp Leu
    850                 855                 860
Glu Lys Glu Glu Arg Phe Leu Lys Pro Asp Val Arg Leu Ser Arg Gly
865                 870                 875                 880
Ser Ile Asp Arg Glu Asp Gly Ser Phe Gln Gly Pro Thr Gly Asn Gln
                885                 890                 895
His Ile Tyr Gln Pro Val Gly Lys Pro Asp Pro Ala Ala Pro Pro Lys
            900                 905                 910
Lys Pro Pro Arg Pro Gly Ala Pro Gly His Leu Ser Asn Leu Ser Ser
```

```
                915                 920                 925
Ile Ser Ser Pro Ala Asp Ser Tyr Asn Glu Gly Val Lys Leu Gln Pro
            930                 935                 940

Gln Glu Ile Ser Pro Pro Thr Ala Asn Leu Asp Arg Ser Asn Asp
945                 950                 955                 960

Lys Val Tyr Glu Asn Val Thr Gly Leu Val Lys Ala Val Ile Glu Met
                965                 970                 975

Ser Ser Lys Ile Gln Pro Ala Pro Pro Glu Glu Tyr Val Pro Met Val
            980                 985                 990

Lys Glu Val Gly Leu Ala Leu Arg Thr Leu Leu Ala Thr Val Asp Glu
                995                 1000                1005

Thr Ile Pro Ala Leu Pro Ala Ser Thr His Arg Glu Ile Glu Met
    1010                1015                1020

Ala Gln Lys Leu Leu Asn Ser Asp Leu Gly Glu Leu Ile Ser Lys
    1025                1030                1035

Met Lys Leu Ala Gln Gln Tyr Val Met Thr Ser Leu Gln Gln Glu
    1040                1045                1050

Tyr Lys Lys Gln Met Leu Thr Ala Ala His Ala Leu Ala Val Asp
    1055                1060                1065

Ala Lys Asn Leu Leu Asp Val Ile Asp Gln Ala Arg Leu Lys Met
    1070                1075                1080

Leu Gly Gln Thr Arg Pro His
    1085                1090

<210> SEQ ID NO 12
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 12

Cys Asp Glu Arg Ser Trp Val Tyr Ser Pro Leu His Tyr Ser Ala Arg
1               5                   10                  15

<210> SEQ ID NO 13
<211> LENGTH: 798
<212> TYPE: PRT
<213> ORGANISM: Mus musculus

<400> SEQUENCE: 13

Met Asn Leu Gln Leu Val Ser Trp Ile Gly Leu Ile Ser Leu Ile Cys
1               5                   10                  15

Ser Val Phe Gly Gln Thr Asp Lys Asn Arg Cys Leu Lys Ala Asn Ala
                20                  25                  30

Lys Ser Cys Gly Glu Cys Ile Gln Ala Gly Pro Asn Cys Gly Trp Cys
            35                  40                  45

Thr Asn Thr Thr Phe Leu Gln Glu Gly Met Pro Thr Ser Ala Arg Cys
        50                  55                  60

Asp Asp Leu Glu Ala Leu Lys Lys Lys Gly Cys Gln Pro Ser Asp Ile
65                  70                  75                  80

Glu Asn Pro Arg Gly Ser Gln Thr Ile Lys Lys Asn Lys Asn Val Thr
                85                  90                  95

Asn Arg Ser Lys Gly Met Ala Glu Lys Leu Arg Pro Glu Asp Ile Thr
            100                 105                 110

Gln Ile Gln Pro Gln Gln Leu Leu Leu Lys Leu Arg Ser Gly Glu Pro
        115                 120                 125
```

```
Gln Lys Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205

Ser Glu Gln Asn Cys Thr Ser Pro Phe Ser Tyr Lys Asn Val Leu Ser
    210                 215                 220

Leu Thr Asp Arg Gly Glu Phe Phe Asn Glu Leu Val Gly Gln Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
        275                 280                 285

Lys Leu Gly Gly Ile Val Leu Pro Asn Asp Gly Gln Cys His Leu Glu
    290                 295                 300

Asn Asn Val Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Gly Asn Ser Ser Asn Val Ile
        355                 360                 365

Gln Leu Ile Ile Asp Ala Tyr Asn Ser Leu Ser Ser Glu Val Ile Leu
    370                 375                 380

Glu Asn Ser Lys Leu Pro Asp Gly Val Thr Ile Asn Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ala
            420                 425                 430

Asn Lys Cys Pro Asn Lys Glu Ser Glu Thr Ile Lys Ile Lys Pro Leu
        435                 440                 445

Gly Phe Thr Glu Glu Val Glu Val Val Leu Gln Phe Ile Cys Lys Cys
    450                 455                 460

Asn Cys Gln Ser His Gly Ile Pro Ala Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
            500                 505                 510

Asp Ala Tyr Cys Arg Lys Glu Asn Ser Ser Glu Ile Cys Ser Asn Asn
        515                 520                 525

Gly Glu Cys Val Cys Gly Gln Cys Val Cys Arg Lys Arg Asp Asn Thr
    530                 535                 540
```

-continued

```
Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Arg Cys
                565                 570                 575

Arg Val Cys Glu Cys Tyr Pro Asn Tyr Thr Gly Ser Ala Cys Asp Cys
            580                 585                 590

Ser Leu Asp Thr Gly Pro Cys Leu Ala Ser Asn Gly Gln Ile Cys Asn
        595                 600                 605

Gly Arg Gly Ile Cys Glu Cys Gly Ala Cys Lys Cys Thr Asp Pro Lys
    610                 615                 620

Phe Gln Gly Pro Thr Cys Glu Thr Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Ala Gln Glu Cys Ser His Phe Asn Leu Thr Lys
                660                 665                 670

Val Glu Ser Arg Glu Lys Leu Pro Gln Pro Val Gln Val Asp Pro Val
            675                 680                 685

Thr His Cys Lys Glu Lys Asp Ile Asp Asp Cys Trp Phe Tyr Phe Thr
        690                 695                 700

Tyr Ser Val Asn Gly Asn Asn Glu Ala Ile Val His Val Val Glu Thr
705                 710                 715                 720

Pro Asp Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
                740                 745                 750

Leu Leu Met Ile Ile His Asp Arg Arg Glu Phe Ala Lys Phe Glu Lys
            755                 760                 765

Glu Lys Met Asn Ala Lys Trp Asp Thr Gly Glu Asn Pro Ile Tyr Lys
        770                 775                 780

Ser Ala Val Thr Thr Val Val Asn Pro Lys Tyr Glu Gly Lys
785                 790                 795

<210> SEQ ID NO 14
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 14

Cys Met Asn Ala Lys Trp Asp Thr Gly Glu Asn Pro Ile Tyr Lys Ser
1               5                   10                  15

Ala

<210> SEQ ID NO 15
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 15
caaaatgcac cttaagttcg ccctcaaggg ctccac                              36

<210> SEQ ID NO 16
<211> LENGTH: 34
<212> TYPE: DNA
```

-continued

```
<213> ORGANISM: Artificial Sequence
<220> FEATURE:
<223> OTHER INFORMATION: Synthetic Oligonucleotide

<400> SEQUENCE: 16
gtacgtggag cccttgaggg cgaacttaac ctgc                                   34

<210> SEQ ID NO 17
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 17
ctatgcacct gttgccttcc gctacttc                                          28

<210> SEQ ID NO 18
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 18
ggccgtggaa tacagagcct tc                                                22

<210> SEQ ID NO 19
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 19
gcgtgaacgg ttcaagcgct tcacgtgcaa cacag                                  35

<210> SEQ ID NO 20
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 20
cttaaatact gtgttgacca tgaagcgctg g                                      31

<210> SEQ ID NO 21
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 21
cccttaagca gtgaaacaca gtactcagtt g                                      31

<210> SEQ ID NO 22
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 22
cccccacgtg ggtgaactct gactctg                                           27
```

<210> SEQ ID NO 23
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 23
gctcaagctt cgaattctcc caccgacgag agg                                    33

<210> SEQ ID NO 24
<211> LENGTH: 641
<212> TYPE: PRT
<213> ORGANISM: Mus musculus

<400> SEQUENCE: 24

Met Glu Leu Glu Val Pro Asp Glu Ala Glu Ser Ala Glu Ala Gly Ala
1               5                   10                  15

Val Thr Ala Glu Ala Ala Trp Ser Ala Glu Ser Gly Ala Ala Ala Gly
            20                  25                  30

Met Thr Gln Lys Lys Ala Gly Leu Ala Glu Ala Pro Leu Val Thr Gly
        35                  40                  45

Gln Pro Gly Pro Gly His Gly Lys Lys Leu Gly His Arg Gly Val Asp
    50                  55                  60

Ala Ser Gly Glu Thr Thr Tyr Lys Lys Thr Thr Ser Ser Thr Leu Lys
65                  70                  75                  80

Gly Ala Ile Gln Leu Gly Ile Gly Tyr Thr Val Gly Asn Leu Ser Ser
                85                  90                  95

Lys Pro Glu Arg Asp Val Leu Met Gln Asp Phe Tyr Val Met Glu Ser
            100                 105                 110

Ile Phe Phe Pro Ser Glu Gly Ser Asn Phe Thr Pro Ala His His Phe
        115                 120                 125

Gln Asp Phe Arg Phe Lys Thr Tyr Ala Pro Val Ala Phe Arg Tyr Phe
    130                 135                 140

Arg Glu Leu Phe Gly Ile Arg Pro Asp Asp Tyr Leu Tyr Ser Leu Cys
145                 150                 155                 160

Asn Glu Pro Leu Ile Glu Leu Ser Asn Pro Gly Ala Ser Gly Ser Val
                165                 170                 175

Phe Tyr Val Thr Ser Asp Asp Glu Phe Ile Ile Lys Thr Val Met His
            180                 185                 190

Lys Glu Ala Glu Phe Leu Gln Lys Leu Leu Pro Gly Tyr Tyr Met Asn
        195                 200                 205

Leu Asn Gln Asn Pro Arg Thr Leu Leu Pro Lys Phe Tyr Gly Leu Tyr
    210                 215                 220

Cys Val Gln Ser Gly Gly Lys Asn Ile Arg Val Val Val Met Asn Asn
225                 230                 235                 240

Val Leu Pro Arg Val Val Lys Met His Leu Lys Phe Asp Leu Lys Gly
                245                 250                 255

Ser Thr Tyr Lys Arg Arg Ala Ser Lys Glu Lys Glu Lys Ser Leu
            260                 265                 270

Pro Thr Tyr Lys Asp Leu Asp Phe Met Gln Asp Met Pro Glu Gly Leu
        275                 280                 285

Leu Leu Asp Ser Asp Thr Phe Gly Ala Leu Val Lys Thr Leu Gln Arg
    290                 295                 300

Asp Cys Leu Val Leu Glu Ser Phe Lys Ile Met Asp Tyr Ser Leu Leu

```
            305                 310                 315                 320
Leu Gly Val His Asn Ile Asp Gln Gln Glu Arg Glu Arg Gln Ala Glu
                325                 330                 335
Gly Ala Gln Ser Lys Ala Asp Glu Lys Arg Pro Val Ala Gln Lys Ala
            340                 345                 350
Leu Tyr Ser Thr Ala Met Glu Ser Ile Gln Gly Ala Ala Arg Gly
        355                 360                 365
Glu Ala Ile Glu Thr Asp Asp Thr Met Gly Gly Ile Pro Ala Val Asn
        370                 375                 380
Gly Arg Gly Glu Arg Leu Leu His Ile Gly Ile Asp Ile Leu
385                 390                 395                 400
Gln Ser Tyr Arg Phe Ile Lys Lys Leu Glu His Thr Trp Lys Ala Leu
                405                 410                 415
Val His Asp Gly Asp Thr Val Ser Val His Arg Pro Ser Phe Tyr Ala
            420                 425                 430
Glu Arg Phe Phe Lys Phe Met Ser Thr Val Phe Arg Lys Ser Ser
        435                 440                 445
Ser Leu Lys Ser Ser Pro Ser Lys Lys Gly Arg Gly Ala Leu Leu Ala
    450                 455                 460
Val Lys Pro Leu Gly Pro Thr Ala Ala Phe Ser Ala Ser Gln Ile Pro
465                 470                 475                 480
Ser Glu Arg Glu Asp Val Gln Tyr Asp Leu Arg Gly Ala Arg Ser Tyr
                485                 490                 495
Pro Thr Leu Glu Asp Glu Gly Arg Pro Asp Leu Leu Pro Cys Thr Pro
            500                 505                 510
Pro Ser Phe Glu Glu Ala Thr Thr Ala Ser Ile Ala Thr Thr Leu Ser
        515                 520                 525
Ser Thr Ser Leu Ser Ile Pro Glu Arg Ser Pro Ser Asp Thr Ser Glu
    530                 535                 540
Gln Pro Arg Tyr Arg Arg Thr Gln Ser Ser Gly Gln Asp Gly Arg
545                 550                 555                 560
Pro Gln Glu Glu Pro His Ala Glu Asp Leu Gln Lys Ile Thr Val Gln
                565                 570                 575
Val Glu Pro Val Cys Gly Val Gly Val Val Pro Lys Glu Glu Gly Ala
            580                 585                 590
Gly Val Glu Val Pro Pro Cys Gly Ala Ser Ala Ala Ser Val Glu
        595                 600                 605
Ile Asp Ala Ala Ser Gln Ala Ser Glu Pro Ala Ser Gln Ala Ser Asp
    610                 615                 620
Glu Glu Asp Ala Pro Ser Thr Asp Ile Tyr Phe Pro Thr Asp Glu Arg
625                 630                 635                 640
Ser

<210> SEQ ID NO 25
<211> LENGTH: 648
<212> TYPE: PRT
<213> ORGANISM: Mus musculus

<400> SEQUENCE: 25

Met Glu Leu Glu Val Pro Asp Glu Ala Glu Ser Ala Glu Ala Gly Ala
1               5                   10                  15
Val Thr Ala Glu Ala Ala Trp Ser Ala Glu Ser Gly Ala Ala Ala Gly
                20                  25                  30
Met Thr Gln Lys Lys Ala Gly Leu Ala Glu Ala Pro Leu Val Thr Gly
```

```
                  35                  40                  45
Gln Pro Gly Pro Gly His Gly Lys Lys Leu His Arg Gly Val Asp
             50                  55                  60
Ala Ser Gly Glu Thr Thr Tyr Lys Lys Thr Thr Ser Ser Thr Leu Lys
 65                  70                  75                  80
Gly Ala Ile Gln Leu Gly Ile Gly Tyr Thr Val Gly Asn Leu Ser Ser
                 85                  90                  95
Lys Pro Glu Arg Asp Val Leu Met Gln Asp Phe Tyr Val Met Glu Ser
             100                 105                 110
Ile Phe Phe Pro Ser Glu Gly Ser Asn Phe Thr Pro Ala His His Phe
             115                 120                 125
Gln Asp Phe Arg Phe Lys Thr Tyr Ala Pro Val Ala Phe Arg Tyr Phe
             130                 135                 140
Arg Glu Leu Phe Gly Ile Arg Pro Asp Asp Tyr Leu Tyr Ser Leu Cys
145                 150                 155                 160
Asn Glu Pro Leu Ile Glu Leu Ser Asn Pro Gly Ala Ser Gly Ser Val
                 165                 170                 175
Phe Tyr Val Thr Ser Asp Asp Glu Phe Ile Ile Lys Thr Val Met His
             180                 185                 190
Lys Glu Ala Glu Phe Leu Gln Lys Leu Leu Pro Gly Tyr Tyr Met Asn
             195                 200                 205
Leu Asn Gln Asn Pro Arg Thr Leu Leu Pro Lys Phe Tyr Gly Leu Tyr
             210                 215                 220
Cys Val Gln Ser Gly Gly Lys Asn Ile Arg Val Val Met Asn Asn
225                 230                 235                 240
Val Leu Pro Arg Val Val Lys Met His Leu Lys Phe Asp Leu Lys Gly
                 245                 250                 255
Ser Thr Tyr Lys Arg Arg Ala Ser Lys Lys Glu Lys Glu Lys Ser Leu
                 260                 265                 270
Pro Thr Tyr Lys Asp Leu Asp Phe Met Gln Asp Met Pro Glu Gly Leu
             275                 280                 285
Leu Leu Asp Ser Asp Thr Phe Gly Ala Leu Val Lys Thr Leu Gln Arg
             290                 295                 300
Asp Cys Leu Val Leu Glu Ser Phe Lys Ile Met Asp Tyr Ser Leu Leu
305                 310                 315                 320
Leu Gly Val His Asn Ile Asp Gln Gln Glu Arg Glu Arg Gln Ala Glu
                 325                 330                 335
Gly Ala Gln Ser Lys Ala Asp Glu Lys Arg Pro Val Ala Gln Lys Ala
             340                 345                 350
Leu Tyr Ser Thr Ala Met Glu Ser Ile Gln Gly Gly Ala Ala Arg Gly
             355                 360                 365
Glu Ala Ile Glu Thr Asp Asp Thr Met Gly Gly Ile Pro Ala Val Asn
             370                 375                 380
Gly Arg Gly Glu Arg Leu Leu Leu His Ile Gly Ile Ile Asp Ile Leu
385                 390                 395                 400
Gln Ser Tyr Arg Phe Ile Lys Lys Leu Glu His Thr Trp Lys Ala Leu
                 405                 410                 415
Val His Asp Gly Asp Thr Val Ser Val His Arg Pro Ser Phe Tyr Ala
                 420                 425                 430
Glu Arg Phe Phe Lys Phe Met Ser Ser Thr Val Phe Arg Lys Ser Ser
             435                 440                 445
Ser Leu Lys Ser Ser Pro Ser Lys Lys Gly Arg Gly Ala Leu Leu Ala
450                 455                 460
```

```
Val Lys Pro Leu Gly Pro Thr Ala Ala Phe Ser Ala Ser Gln Ile Pro
465                 470                 475                 480

Ser Glu Arg Glu Asp Val Gln Tyr Asp Leu Arg Gly Ala Arg Ser Tyr
                485                 490                 495

Pro Thr Leu Glu Asp Glu Gly Arg Pro Asp Leu Leu Pro Cys Thr Pro
            500                 505                 510

Pro Ser Phe Glu Glu Ala Thr Thr Ala Ser Ile Ala Thr Thr Leu Ser
        515                 520                 525

Ser Thr Ser Leu Ser Ile Pro Glu Arg Ser Pro Ser Asp Thr Ser Glu
    530                 535                 540

Gln Pro Arg Tyr Arg Arg Thr Gln Ser Ser Gly Gln Asp Gly Arg
545                 550                 555                 560

Pro Gln Glu Glu Pro His Ala Glu Asp Leu Gln Lys Ile Thr Val Gln
                565                 570                 575

Val Glu Pro Val Cys Gly Val Gly Val Pro Lys Glu Glu Gly Ala
                580                 585                 590

Gly Val Glu Val Pro Pro Cys Gly Ala Ser Ala Ala Ser Val Glu
            595                 600                 605

Ile Asp Ala Ala Ser Gln Ala Ser Glu Pro Ala Ser Gln Ala Ser Asp
        610                 615                 620

Glu Glu Asp Ala Pro Ser Thr Asp Ile Tyr Phe Pro Thr Asp Glu Arg
625                 630                 635                 640

Ser Trp Val Tyr Ser Pro Leu His
                645

<210> SEQ ID NO 26
<211> LENGTH: 657
<212> TYPE: PRT
<213> ORGANISM: Mus musculus

<400> SEQUENCE: 26

Met Glu Leu Glu Val Pro Asp Glu Ala Glu Ser Ala Glu Ala Gly Ala
1               5                   10                  15

Val Thr Ala Glu Ala Ala Trp Ser Glu Ser Gly Ala Ala Gly
            20                  25                  30

Met Thr Gln Lys Lys Ala Gly Leu Ala Glu Ala Pro Leu Val Thr Gly
            35                  40                  45

Gln Pro Gly Pro Gly His Gly Lys Lys Leu Gly His Arg Gly Val Asp
        50                  55                  60

Ala Ser Gly Glu Thr Thr Tyr Lys Lys Thr Thr Ser Ser Thr Leu Lys
65                  70                  75                  80

Gly Ala Ile Gln Leu Gly Ile Gly Tyr Thr Val Gly Asn Leu Ser Ser
                85                  90                  95

Lys Pro Glu Arg Asp Val Leu Met Gln Asp Phe Tyr Val Met Glu Ser
                100                 105                 110

Ile Phe Phe Pro Ser Glu Gly Ser Asn Phe Thr Pro Ala His His Phe
        115                 120                 125

Gln Asp Phe Arg Phe Lys Thr Tyr Ala Pro Val Ala Phe Arg Tyr Phe
    130                 135                 140

Arg Glu Leu Phe Gly Ile Arg Pro Asp Asp Tyr Leu Tyr Ser Leu Cys
145                 150                 155                 160

Asn Glu Pro Leu Ile Glu Leu Ser Asn Pro Gly Ala Ser Gly Ser Val
                165                 170                 175

Phe Tyr Val Thr Ser Asp Asp Glu Phe Ile Ile Lys Thr Val Met His
```

-continued

```
                180                 185                 190
Lys Glu Ala Glu Phe Leu Gln Lys Leu Leu Pro Gly Tyr Tyr Met Asn
            195                 200                 205
Leu Asn Gln Asn Pro Arg Thr Leu Leu Pro Lys Phe Tyr Gly Leu Tyr
        210                 215                 220
Cys Val Gln Ser Gly Gly Lys Asn Ile Arg Val Val Met Asn Asn
225                 230                 235                 240
Val Leu Pro Arg Val Val Lys Met His Leu Lys Phe Asp Leu Lys Gly
                245                 250                 255
Ser Thr Tyr Lys Arg Arg Ala Ser Lys Lys Glu Lys Glu Lys Ser Leu
            260                 265                 270
Pro Thr Tyr Lys Asp Leu Asp Phe Met Gln Asp Met Pro Glu Gly Leu
            275                 280                 285
Leu Leu Asp Ser Asp Thr Phe Gly Ala Leu Val Lys Thr Leu Gln Arg
        290                 295                 300
Asp Cys Leu Val Leu Glu Ser Phe Lys Ile Met Asp Tyr Ser Leu Leu
305                 310                 315                 320
Leu Gly Val His Asn Ile Asp Gln Gln Glu Arg Glu Arg Gln Ala Glu
                325                 330                 335
Gly Ala Gln Ser Lys Ala Asp Glu Lys Arg Pro Val Ala Gln Lys Ala
            340                 345                 350
Leu Tyr Ser Thr Ala Met Glu Ser Ile Gln Gly Gly Ala Ala Arg Gly
            355                 360                 365
Glu Ala Ile Glu Thr Asp Asp Thr Met Gly Gly Ile Pro Ala Val Asn
        370                 375                 380
Gly Arg Gly Glu Arg Leu Leu His Ile Gly Ile Asp Ile Leu
385                 390                 395                 400
Gln Ser Tyr Arg Phe Ile Lys Lys Leu Glu His Thr Trp Lys Ala Leu
                405                 410                 415
Val His Asp Gly Asp Thr Val Ser Val His Arg Pro Ser Phe Tyr Ala
            420                 425                 430
Glu Arg Phe Phe Lys Phe Met Ser Ser Thr Val Phe Arg Lys Ser Ser
        435                 440                 445
Ser Leu Lys Ser Ser Pro Ser Lys Lys Gly Arg Gly Ala Leu Leu Ala
        450                 455                 460
Val Lys Pro Leu Gly Pro Thr Ala Ala Phe Ser Ala Ser Gln Ile Pro
465                 470                 475                 480
Ser Glu Arg Glu Asp Val Gln Tyr Asp Leu Arg Gly Ala Arg Ser Tyr
                485                 490                 495
Pro Thr Leu Glu Asp Glu Gly Arg Pro Asp Leu Leu Pro Cys Thr Pro
            500                 505                 510
Pro Ser Phe Glu Glu Ala Thr Ala Ser Ile Ala Thr Thr Leu Ser
        515                 520                 525
Ser Thr Ser Leu Ser Ile Pro Glu Arg Ser Pro Ser Asp Thr Ser Glu
        530                 535                 540
Gln Pro Arg Tyr Arg Arg Arg Thr Gln Ser Ser Gly Gln Asp Gly Arg
545                 550                 555                 560
Pro Gln Glu Glu Pro His Ala Glu Asp Leu Gln Lys Ile Thr Val Gln
                565                 570                 575
Val Glu Pro Val Cys Gly Val Gly Val Pro Lys Glu Glu Gly Ala
            580                 585                 590
Gly Val Glu Val Pro Pro Cys Gly Ala Ser Ala Ala Ser Val Glu
        595                 600                 605
```

```
Ile Asp Ala Ala Ser Gln Ala Ser Glu Pro Ala Ser Gln Ala Ser Asp
    610                 615                 620

Glu Glu Asp Ala Pro Ser Thr Asp Ile Tyr Phe Pro Thr Asp Glu Arg
625                 630                 635                 640

Ser Trp Val Tyr Ser Pro Leu His Tyr Ser Ala Arg Pro Ala Ser Asp
                645                 650                 655

Gly

<210> SEQ ID NO 27
<211> LENGTH: 661
<212> TYPE: PRT
<213> ORGANISM: Mus musculus

<400> SEQUENCE: 27

Met Glu Leu Glu Val Pro Asp Glu Ala Glu Ser Ala Glu Ala Gly Ala
1               5                   10                  15

Val Thr Ala Glu Ala Ala Trp Ser Glu Ser Gly Ala Ala Gly
            20                  25                  30

Met Thr Gln Lys Lys Ala Gly Leu Ala Glu Ala Pro Leu Val Thr Gly
                35                  40                  45

Gln Pro Gly Pro Gly His Gly Lys Lys Leu Gly His Arg Gly Val Asp
    50                  55                  60

Ala Ser Gly Glu Thr Thr Tyr Lys Lys Thr Thr Ser Ser Thr Leu Lys
65                  70                  75                  80

Gly Ala Ile Gln Leu Gly Ile Gly Tyr Thr Val Gly Asn Leu Ser Ser
                85                  90                  95

Lys Pro Glu Arg Asp Val Leu Met Gln Asp Phe Tyr Val Met Glu Ser
            100                 105                 110

Ile Phe Phe Pro Ser Glu Gly Ser Asn Phe Thr Pro Ala His His Phe
            115                 120                 125

Gln Asp Phe Arg Phe Lys Thr Tyr Ala Pro Val Ala Phe Arg Tyr Phe
    130                 135                 140

Arg Glu Leu Phe Gly Ile Arg Pro Asp Asp Tyr Leu Tyr Ser Leu Cys
145                 150                 155                 160

Asn Glu Pro Leu Ile Glu Leu Ser Asn Pro Gly Ala Ser Gly Ser Val
                165                 170                 175

Phe Tyr Val Thr Ser Asp Asp Glu Phe Ile Ile Lys Thr Val Met His
            180                 185                 190

Lys Glu Ala Glu Phe Leu Gln Lys Leu Leu Pro Gly Tyr Tyr Met Asn
            195                 200                 205

Leu Asn Gln Asn Pro Arg Thr Leu Leu Pro Lys Phe Tyr Gly Leu Tyr
    210                 215                 220

Cys Val Gln Ser Gly Gly Lys Asn Ile Arg Val Val Met Asn Asn
225                 230                 235                 240

Val Leu Pro Arg Val Val Lys Met His Leu Lys Phe Asp Leu Lys Gly
                245                 250                 255

Ser Thr Tyr Lys Arg Arg Ala Ser Lys Lys Glu Lys Ser Leu
            260                 265                 270

Pro Thr Tyr Lys Asp Leu Asp Phe Met Gln Asp Met Pro Glu Gly Leu
            275                 280                 285

Leu Leu Asp Ser Asp Thr Phe Gly Ala Leu Val Lys Thr Leu Gln Arg
    290                 295                 300

Asp Cys Leu Val Leu Glu Ser Phe Lys Ile Met Asp Tyr Ser Leu Leu
305                 310                 315                 320
```

Leu Gly Val His Asn Ile Asp Gln Gln Glu Arg Glu Arg Gln Ala Glu
            325                 330                 335

Gly Ala Gln Ser Lys Ala Asp Glu Lys Arg Pro Val Ala Gln Lys Ala
        340                 345                 350

Leu Tyr Ser Thr Ala Met Glu Ser Ile Gln Gly Gly Ala Ala Arg Gly
    355                 360                 365

Glu Ala Ile Glu Thr Asp Asp Thr Met Gly Gly Ile Pro Ala Val Asn
370                 375                 380

Gly Arg Gly Glu Arg Leu Leu His Ile Gly Ile Asp Ile Leu
385                 390                 395                 400

Gln Ser Tyr Arg Phe Ile Lys Lys Leu Glu His Thr Trp Lys Ala Leu
                405                 410                 415

Val His Asp Gly Asp Thr Val Ser Val His Arg Pro Ser Phe Tyr Ala
            420                 425                 430

Glu Arg Phe Phe Lys Phe Met Ser Ser Thr Val Phe Arg Lys Ser Ser
        435                 440                 445

Ser Leu Lys Ser Ser Pro Ser Lys Lys Gly Arg Gly Ala Leu Leu Ala
    450                 455                 460

Val Lys Pro Leu Gly Pro Thr Ala Ala Phe Ser Ala Ser Gln Ile Pro
465                 470                 475                 480

Ser Glu Arg Glu Asp Val Gln Tyr Asp Leu Arg Gly Ala Arg Ser Tyr
                485                 490                 495

Pro Thr Leu Glu Asp Glu Gly Arg Pro Asp Leu Leu Pro Cys Thr Pro
            500                 505                 510

Pro Ser Phe Glu Glu Ala Thr Thr Ala Ser Ile Ala Thr Thr Leu Ser
        515                 520                 525

Ser Thr Ser Leu Ser Ile Pro Glu Arg Ser Pro Ser Asp Thr Ser Glu
    530                 535                 540

Gln Pro Arg Tyr Arg Arg Thr Gln Ser Ser Gly Gln Asp Gly Arg
545                 550                 555                 560

Pro Gln Glu Glu Pro His Ala Glu Asp Leu Gln Lys Ile Thr Val Gln
                565                 570                 575

Val Glu Pro Val Cys Gly Val Gly Val Val Pro Lys Glu Glu Gly Ala
            580                 585                 590

Gly Val Glu Val Pro Pro Cys Gly Ala Ser Ala Ala Ser Val Glu
        595                 600                 605

Ile Asp Ala Ala Ser Gln Ala Ser Glu Pro Ala Ser Gln Ala Ser Asp
    610                 615                 620

Glu Glu Asp Ala Pro Ser Thr Asp Ile Tyr Phe Pro Thr Asp Glu Arg
625                 630                 635                 640

Ser Trp Val Phe Ser Pro Leu His Tyr Ser Ala Arg Pro Ala Ser Asp
                645                 650                 655

Gly Glu Ser Asp Thr
            660

<210> SEQ ID NO 28
<211> LENGTH: 661
<212> TYPE: PRT
<213> ORGANISM: Mus musculus

<400> SEQUENCE: 28

Met Glu Leu Glu Val Pro Asp Glu Ala Glu Ser Ala Glu Ala Gly Ala
1               5                   10                  15

Val Thr Ala Glu Ala Ala Trp Ser Ala Glu Ser Gly Ala Ala Ala Gly

-continued

```
                20                  25                  30
Met Thr Gln Lys Lys Ala Gly Leu Ala Glu Ala Pro Leu Val Thr Gly
             35                  40                  45

Gln Pro Gly Pro Gly His Gly Lys Lys Leu Gly His Arg Gly Val Asp
         50                  55                  60

Ala Ser Gly Glu Thr Thr Tyr Lys Lys Thr Thr Ser Ser Thr Leu Lys
 65                  70                  75                  80

Gly Ala Ile Gln Leu Gly Ile Gly Tyr Thr Val Gly Asn Leu Ser Ser
                 85                  90                  95

Lys Pro Glu Arg Asp Val Leu Met Gln Asp Phe Tyr Val Met Glu Ser
            100                 105                 110

Ile Phe Phe Pro Ser Glu Gly Ser Asn Phe Thr Pro Ala His His Phe
            115                 120                 125

Gln Asp Phe Arg Phe Lys Thr Tyr Ala Pro Val Ala Phe Arg Tyr Phe
            130                 135                 140

Arg Glu Leu Phe Gly Ile Arg Pro Asp Asp Tyr Leu Tyr Ser Leu Cys
145                 150                 155                 160

Asn Glu Pro Leu Ile Glu Leu Ser Asn Pro Gly Ala Ser Gly Ser Val
                165                 170                 175

Phe Tyr Val Thr Ser Asp Asp Glu Phe Ile Ile Lys Thr Val Met His
                180                 185                 190

Lys Glu Ala Glu Phe Leu Gln Lys Leu Leu Pro Gly Tyr Tyr Met Asn
            195                 200                 205

Leu Asn Gln Asn Pro Arg Thr Leu Leu Pro Lys Phe Tyr Gly Leu Tyr
            210                 215                 220

Cys Val Gln Ser Gly Gly Lys Asn Ile Arg Val Val Met Asn Asn
225                 230                 235                 240

Val Leu Pro Arg Val Val Lys Met His Leu Lys Phe Asp Leu Lys Gly
                245                 250                 255

Ser Thr Tyr Lys Arg Arg Ala Ser Lys Lys Glu Lys Glu Lys Ser Leu
            260                 265                 270

Pro Thr Tyr Lys Asp Leu Asp Phe Met Gln Asp Met Pro Glu Gly Leu
            275                 280                 285

Leu Leu Asp Ser Asp Thr Phe Gly Ala Leu Val Lys Thr Leu Gln Arg
290                 295                 300

Asp Cys Leu Val Leu Glu Ser Phe Lys Ile Met Asp Tyr Ser Leu Leu
305                 310                 315                 320

Leu Gly Val His Asn Ile Asp Gln Gln Glu Arg Glu Arg Gln Ala Glu
                325                 330                 335

Gly Ala Gln Ser Lys Ala Asp Glu Lys Arg Pro Val Ala Gln Lys Ala
                340                 345                 350

Leu Tyr Ser Thr Ala Met Glu Ser Ile Gln Gly Ala Ala Arg Gly
            355                 360                 365

Glu Ala Ile Glu Thr Asp Asp Thr Met Gly Gly Ile Pro Ala Val Asn
            370                 375                 380

Gly Arg Gly Glu Arg Leu Leu His Ile Gly Ile Asp Ile Leu
385                 390                 395                 400

Gln Ser Tyr Arg Phe Ile Lys Lys Leu Glu His Thr Trp Lys Ala Leu
                405                 410                 415

Val His Asp Gly Asp Thr Val Ser Val His Arg Pro Ser Phe Tyr Ala
            420                 425                 430

Glu Arg Phe Phe Lys Phe Met Ser Ser Thr Val Phe Arg Lys Ser Ser
            435                 440                 445
```

-continued

```
Ser Leu Lys Ser Ser Pro Ser Lys Gly Arg Gly Ala Leu Leu Ala
    450                 455                 460

Val Lys Pro Leu Gly Pro Thr Ala Ala Phe Ala Ser Gln Ile Pro
465                 470                 475                 480

Ser Glu Arg Glu Asp Val Gln Tyr Asp Leu Arg Gly Ala Arg Ser Tyr
                    485                 490                 495

Pro Thr Leu Glu Asp Glu Gly Arg Pro Asp Leu Leu Pro Cys Thr Pro
                500                 505                 510

Pro Ser Phe Glu Glu Ala Thr Thr Ala Ser Ile Ala Thr Thr Leu Ser
            515                 520                 525

Ser Thr Ser Leu Ser Ile Pro Glu Arg Ser Pro Ser Asp Thr Ser Glu
    530                 535                 540

Gln Pro Arg Tyr Arg Arg Thr Gln Ser Ser Gly Gln Asp Gly Arg
545                 550                 555                 560

Pro Gln Glu Glu Pro His Ala Glu Asp Leu Gln Lys Ile Thr Val Gln
                565                 570                 575

Val Glu Pro Val Cys Gly Val Gly Val Val Pro Lys Glu Glu Gly Ala
                580                 585                 590

Gly Val Glu Val Pro Pro Cys Gly Ala Ser Ala Ala Ser Val Glu
            595                 600                 605

Ile Asp Ala Ala Ser Gln Ala Ser Glu Pro Ala Ser Gln Ala Ser Asp
    610                 615                 620

Glu Glu Asp Ala Pro Ser Thr Asp Ile Tyr Phe Pro Thr Asp Glu Arg
625                 630                 635                 640

Ser Trp Val Tyr Ser Pro Leu His Phe Ser Ala Arg Pro Ala Ser Asp
                    645                 650                 655

Gly Glu Ser Asp Thr
            660

<210> SEQ ID NO 29
<211> LENGTH: 661
<212> TYPE: PRT
<213> ORGANISM: Mus musculus

<400> SEQUENCE: 29

Met Glu Leu Glu Val Pro Asp Glu Ala Glu Ser Ala Glu Ala Gly Ala
1               5                   10                  15

Val Thr Ala Glu Ala Ala Trp Ser Ala Glu Ser Gly Ala Ala Ala Gly
                20                  25                  30

Met Thr Gln Lys Lys Ala Gly Leu Ala Glu Ala Pro Leu Val Thr Gly
            35                  40                  45

Gln Pro Gly Pro Gly His Gly Lys Lys Leu Gly His Arg Gly Val Asp
        50                  55                  60

Ala Ser Gly Glu Thr Thr Tyr Lys Lys Thr Thr Ser Ser Thr Leu Lys
65                  70                  75                  80

Gly Ala Ile Gln Leu Gly Ile Gly Tyr Thr Val Gly Asn Leu Ser Ser
                85                  90                  95

Lys Pro Glu Arg Asp Val Leu Met Gln Asp Phe Tyr Val Met Glu Ser
                100                 105                 110

Ile Phe Phe Pro Ser Glu Gly Ser Asn Phe Thr Pro Ala His His Phe
            115                 120                 125

Gln Asp Phe Arg Phe Lys Thr Tyr Ala Pro Val Ala Phe Arg Tyr Phe
        130                 135                 140

Arg Glu Leu Phe Gly Ile Arg Pro Asp Asp Tyr Leu Tyr Ser Leu Cys
```

```
            145                 150                 155                 160
Asn Glu Pro Leu Ile Glu Leu Ser Asn Pro Gly Ala Ser Gly Ser Val
                165                 170                 175
Phe Tyr Val Thr Ser Asp Asp Glu Phe Ile Ile Lys Thr Val Met His
            180                 185                 190
Lys Glu Ala Glu Phe Leu Gln Lys Leu Leu Pro Gly Tyr Tyr Met Asn
        195                 200                 205
Leu Asn Gln Asn Pro Arg Thr Leu Leu Pro Lys Phe Tyr Gly Leu Tyr
        210                 215                 220
Cys Val Gln Ser Gly Lys Asn Ile Arg Val Val Met Asn Asn
225                 230                 235                 240
Val Leu Pro Arg Val Lys Met His Leu Lys Phe Asp Leu Lys Gly
                245                 250                 255
Ser Thr Tyr Lys Arg Arg Ala Ser Lys Glu Lys Glu Lys Ser Leu
                260                 265                 270
Pro Thr Tyr Lys Asp Leu Asp Phe Met Gln Asp Met Pro Glu Gly Leu
            275                 280                 285
Leu Leu Asp Ser Asp Thr Phe Gly Ala Leu Val Lys Thr Leu Gln Arg
        290                 295                 300
Asp Cys Leu Val Leu Glu Ser Phe Lys Ile Met Asp Tyr Ser Leu Leu
305                 310                 315                 320
Leu Gly Val His Asn Ile Asp Gln Gln Glu Arg Glu Arg Gln Ala Glu
                325                 330                 335
Gly Ala Gln Ser Lys Ala Asp Glu Lys Arg Pro Val Ala Gln Lys Ala
                340                 345                 350
Leu Tyr Ser Thr Ala Met Glu Ser Ile Gln Gly Gly Ala Ala Arg Gly
                355                 360                 365
Glu Ala Ile Glu Thr Asp Asp Thr Met Gly Gly Ile Pro Ala Val Asn
        370                 375                 380
Gly Arg Gly Glu Arg Leu Leu His Ile Gly Ile Ile Asp Ile Leu
385                 390                 395                 400
Gln Ser Tyr Arg Phe Ile Lys Lys Leu Glu His Thr Trp Lys Ala Leu
                405                 410                 415
Val His Asp Gly Asp Thr Val Ser Val His Arg Pro Ser Phe Tyr Ala
                420                 425                 430
Glu Arg Phe Phe Lys Phe Met Ser Ser Thr Val Phe Arg Lys Ser Ser
            435                 440                 445
Ser Leu Lys Ser Ser Pro Ser Lys Lys Gly Arg Gly Ala Leu Leu Ala
        450                 455                 460
Val Lys Pro Leu Gly Pro Thr Ala Ala Phe Ser Ala Ser Gln Ile Pro
465                 470                 475                 480
Ser Glu Arg Glu Asp Val Gln Tyr Asp Leu Arg Gly Ala Arg Ser Tyr
                485                 490                 495
Pro Thr Leu Glu Asp Glu Gly Arg Pro Asp Leu Leu Pro Cys Thr Pro
            500                 505                 510
Pro Ser Phe Glu Glu Ala Thr Thr Ala Ser Ile Ala Thr Thr Leu Ser
        515                 520                 525
Ser Thr Ser Leu Ser Ile Pro Glu Arg Ser Pro Ser Asp Thr Ser Glu
        530                 535                 540
Gln Pro Arg Tyr Arg Arg Thr Gln Ser Ser Gly Gln Asp Gly Arg
545                 550                 555                 560
Pro Gln Glu Glu Pro His Ala Glu Asp Leu Gln Lys Ile Thr Val Gln
                565                 570                 575
```

-continued

```
Val Glu Pro Val Cys Gly Val Gly Val Val Pro Lys Glu Glu Gly Ala
            580                 585                 590

Gly Val Glu Val Pro Pro Cys Gly Ala Ser Ala Ala Ala Ser Val Glu
        595                 600                 605

Ile Asp Ala Ala Ser Gln Ala Ser Glu Pro Ala Ser Gln Ala Ser Asp
        610                 615                 620

Glu Glu Asp Ala Pro Ser Thr Asp Ile Tyr Phe Pro Thr Asp Glu Arg
625                 630                 635                 640

Ser Trp Val Phe Ser Pro Leu His Phe Ser Ala Arg Pro Ala Ser Asp
                645                 650                 655

Gly Glu Ser Asp Thr
```

METHODS OF PREVENTING OR TREATING CELL MIGRATION MEDIATED CONDITIONS OR DISEASES

INTRODUCTION

This application is a division of U.S. Ser. No. 10/606,038 filed Jun. 25, 2003. This invention was made in the course of research sponsored by the National Institutes of Health (Grant No. GM57549). The U.S. government may have certain rights in this invention.

BACKGROUND OF THE INVENTION

The ability of cells to form cell contacts, adhere to the extracellular matrix, change morphology, and migrate is essential for development, wound healing, metastasis, cell survival and the immune response. These events depend on the binding of integrin to the extracellular matrix, and assembly of focal adhesions, which are complexes of scaffolding and signaling proteins organized by adhesion to the extracellular matrix (Critchley (2000) *Curr. Opin. Cell Biol.* 12:133-139; Burridge and Chrzanowska-Wodnicka (1996) *Annu. Rev. Cell Dev. Biol.* 12:463-518; Schwartz and Ginsberg (2002) *Nature Cell Biol.* 4:E65-E68). Phosphatidylinositol-4,5-bisphosphate (PtdIns(4,5)$P_2$) regulates interactions between these proteins, including the interaction of vinculin with actin and talin (McNamee, et al. (1993) *J. Cell Biol.* 121:673-678; Berditchevski, et al. (1997) *J. Biol. Chem.* 272:2595-2598; Chong, et al. (1994) *Cell* 79:507-513; Gilmore and Burridge (1996) *Nature* 381:531-535; Steimle, et al. (1999) *J. Biol. Chem.* 274:18414-18420; Martel, et al. (2001) *J. Biol. Chem.* 276:21217-21227). The binding of talin to β-integrin is strengthened by PtdIns(4,5)$P_2$, suggesting that the basis of focal adhesion assembly is regulated by this lipid mediator (Martel, et al. (2001) supra; Janmey (1994) *Annu. Rev. Physiol.* 56:169-191). Further, it has been suggested that PIPKIγ661/talin association is important for targeting PIPKIγ661 to focal adhesions (Di Paolo, et al. (2002) *Nature* 420:85-89; Ling, et al. (2002) *Nature* 420:89-93).

SUMMARY OF THE INVENTION

One aspect of the present invention is a method for identifying an agent that modulates the activity of Type I phosphatidylinositol phosphate kinase isoform γ661 (PIPKIγ661). The method involves contacting PIPKIγ661 with a test agent in the presence of at least one selected protein and detecting the activity of PIPKIγ661. A change in the activity of PIPKIγ661 as compared to a control is indicative of said agent modulating the activity of PIPKIγ661. In one preferred embodiment, the agent modulates the activity of Src thereby modulating the activity of PIPKIγ661. In another preferred embodiment, the agent modulates the activity of FAK thereby modulating the activity of PIPKIγ661.

Another aspect of the present invention is a method for identifying an agent that modulates cell focal adhesion assembly. The method involves contacting a cell which lacks active PIPKIγ661 or which overexpresses PIPKIγ661 with a test agent and measuring the adherence of said cell to a surface. A difference in the adherence of the cell to the surface in the presence of the test agent as compared to the adherence of the cell to the surface in the absence of the test agent is indicative of the agent modulating cell focal adhesion assembly.

A further aspect of the present invention is a method of preventing or treating a cell migration-mediated condition or disease in a subject. The method involves administering to a subject an effective amount of an agent that modulates the activity of PIPKIγ661 or cell focal adhesion assembly in a cell which lacks active PIPKIγ661 or which overexpresses PIPKIγ661 so that at least one sign or symptom of a cell migration-mediated condition or disease is prevented or treated.

BRIEF DESCRIPTION OF THE DRAWINGS

FIG. 1 illustrates the epitope-tagged constructs and relative focal adhesion (FA) targeting. c-Myc-tagged constructs are chimeras of PIPKIα and PIPKIγ tail.

FIG. 2 demonstrates the inhibition of talin binding to integrin with PIPKIγ661 peptides PN (diamonds), pY644 (squares), pY649 (circles) and pY644/649 (triangles).

FIG. 3 illustrates constructs of PIPKIγ661 truncations or tyrosine mutations.

DETAILED DESCRIPTION OF THE INVENTION

Adherence to extracellular matrix stimulates the generation of PtdIns(4,5)$P_2$ (McNamee, et al. (1993) supra; Chong, et al. (1994) supra) and may modulate focal adhesion assembly around clusters of integrins (Martel, et al. (2001) supra; Janmey (1994) supra). Type I phosphatidylinositol phosphate kinase isoforms (PIPKIs) generate the lipid messenger PtdIns(4,5)$P_2$ (Anderson, et al. (1999) *J. Biol. Chem.* 274:9907-9910; Kunz, et al. (2000) *Mol. Cell* 5:1-11). The PIPKIγ transcripts are alternatively spliced messenger RNA, resulting in the PIPKIγ635 and PIPKIγ661 isoforms that differ by a 26-amino-acid carboxy-terminal extension (Ishihara, et al. (1998) *J. Biol. Chem.* 273:8741-8748).

It has now been found that the PIPKIγ661 isoform is specifically targeted to focal adhesions by an association with talin. PIPKIγ661 was tyrosine phosphorylated by focal adhesion-associated kinase signaling, increasing both the activity of phosphatidylinositol phosphate kinase and its association with talin.

Immunolocalization studies indicated that PIPKIγ661 was targeted to focal adhesions. To determine whether the C-terminal 26 amino acids of PIPKIγ661 were sufficient for targeting, these residues were fused to green fluorescent protein (GFPγ26). The GFPγ26 fusion protein was poorly targeted to focal adhesions, indicating that other regions within PIPKIγ661 were also required. To define these constraints, chimeras of PIPKIα, an enzyme not targeted to focal adhesions, were produced. The PIPKIα/γ chimeras contained 178 residues from the C-terminus of PIPKIγ661 (PIPKIα/γ661), the 178 residues from the C-terminus of PIPKIγ661 lacking the 26 C-terminal amino acid sequences (PIPKIγ635) or 26 amino acids from the C-terminus of PIPKIγ661 fused to the C-terminus of PIPKIA (PIPKIα/γ26) (FIG. 1). PIPKIα/γ661 and PIPKIα/γ26 were targeted to focal adhesions, whereas PIPKIα/γ635 was not. Enhanced targeting of PIPKIα chimera constructs containing the C-terminal 26 residues reflects structural or functional features of the phosphatidylinositol phosphate kinases, such as dimer formation, which are required for activity at membranes (Kunz, et al. (2000) supra; Rao, et al. (1998) *Cell* 94:829-839).

Two approaches were used to identify proteins that specifically interact with PIPKIγ661. Haemagglutinin (HA)-tagged PIPKIγ661 or PIPKIγ635 were expressed in HEK 293T cells, and isolated by immunoprecipitation. As numerous focal adhesion proteins are tyrosine phosphorylated, the immunoprecipitates were immunoblotted with anti-phosphotyrosine antibodies. A tyrosine-phosphorylated protein of relative molecular mass 230,000 ($M_r$ 230K) was selectively immunoprecipitated with PIPKIγ661. This protein was identified as talin (Pasquale, et al. (1986) *Proc. Natl Acad. Sci. USA* 83:5507-5511; DeClue and Martin (1987) *Mol. Cell Biol.* 7:371-378). Vinculin, focal adhesion-associated kinase (FAK) and tensin did not interact with PIPKIγ661. Only the PIPKIα/γ chimeras that target to focal adhesions associated with talin. To confirm the talin-PIPKIγ661 interaction, talin was immunoprecipitated from HEK293T cells overexpressing PIPKIγ661 or PIPKIγ635. Talin co-precipitated with PIPKIγ661, but not PIPKIγ635. It is known that endogenous PIPKIγ splice isoforms are widely expressed in various cell lines. When endogenous PIPKIγ was immunoprecipitated from a variety of cells types, talin association was consistently observed.

A yeast two-hybrid screen using the 178-residue C-terminal region of PIPKIγ661 as bait resulted in the isolation of 12 talin clones. This demonstrated a direct interaction, and narrowed the interacting region to residues 150 to 480 in the talin head region. This region encompasses a portion of F1 and the F2 and F3 regions of talin's band 4.1, ezrin, radixin, and moesin (FERM) homology domain. The talin FERM domain also contains regions shown to interact with other focal adhesion proteins (Calderwood, et al. (1999) *J. Biol. Chem.* 274:28071-28074; Rees, et al. (1990) *Nature* 347:685-689; Chisti, et al. (1998) *Trends Biochem. Sci.* 23:281-282; Calderwood, et al. (2002) *J. Biol. Chem.* 277: 21749-21758).

These data demonstrate that the PIPKIγ661-talin association is important for targeting PIPKIγ661 to focal adhesions. This interaction was further substantiated by the immunofluorescent colocalization of PIPKIγ661 and talin in NRK cells. As PtdIns(4,5)P$_2$ modulates the association of talin with β-integrin and other focal adhesion proteins (Gilmore and Burridge (1996) supra; Martel, et al. (2001) supra; Janmey (1994) supra), it was determined whether the PIPKIγ661-talin interaction regulates the focal adhesion assembly of talin. Moderate overexpression of PIPKIγ661 resulted in substantially larger talin-containing focal adhesions in 43% of cells compared to non-transfected cells. This indicated that PIPKIγ661 modulates talin assembly into focal adhesions. High overexpression of PIPKIγ661, but not PIPKIγ7635, resulted in a loss of talin from focal adhesions in 49% of the transfected cells. These data indicate that increasing levels of PtdIns(4,5)P$_2$ at focal adhesions cause talin assembly and disassembly. Overexpression of PIPKI isoforms reorganizes actin from stress fibers to cortical actin filaments (Anderson, et al. (1999) supra; Ishihara, et al. (1998) supra). Thus, phenotypes observed by high overexpression of PIPKIγ661 may also affect focal adhesions indirectly.

Expression of a kinase-inactive, also referred to herein as kinase-dead, PIPKIγ661 mutant (PIPKIγ661kd) resulted in a loss of talin targeting to focal adhesions in 70% of the cells expressing high levels. This further indicated a role for PtdIns(4,5)P$_2$ in talin assembly into focal adhesions.

During adhesion and spreading, cells assemble focal adhesions rapidly, providing a good model to define the role of PIPKIγ661 in membrane and focal adhesion assembly of talin. PIPKIγ661 facilitated the targeting of talin to the plasma membrane in adhering cells. This was independent of PIP kinase activity, as PIPKIγ661kd also facilitated targeting. Significantly, PIPKIγ661 facilitated the assembly of talin-containing focal adhesions in spreading cells, and this was dependent on PIP kinase activity. These data show that PIPKIγ661 regulates both plasma membrane targeting and the efficient assembly of talin into focal adhesions.

The association between PIPKIγ661 and talin was also regulated by adhesion to type I collagen. In co-immunoprecipitation of talin with PIPKIγ661 from HEK293T cells in suspension versus cells adherent to type I collagen, it was found that talin strongly associated with PIPKIγ661 in adherent cells, but not in suspended cells. However, in suspended cells, the PIPKIγ661 association with talin was restored when cells were stimulated with lysophosphatidic acid (LPA) or platelet-derived growth factor (PDGF).

Tyrosine phosphorylation of focal adhesion proteins is stimulated by adhesion, and is important for focal adhesion assembly (Cary and Guan (1999) *Front. Biosci.* 4:D102-D113). PIPKIγ661 was tyrosine phosphorylated, and this was dependent upon PIP kinase activity. Tyrosine phosphorylation was also stimulated upon cell adhesion to type I collagen. FAK is an important tyrosine kinase at focal adhesions and is activated by LPA (Rodriquez-Fernandez and Rozengurt (1998) *J. Biol. Chem.* 273:19321-19328). To determine FAK's role in tyrosine phosphorylation of PIPKIγ661, dominant active FAK (CD2FAK) (Chan, et al. (1994) *J. Biol. Chem.* 269:20567-20574) was co-expressed with each of the PIPKIγ isoforms. This induced a 4-fold increase in tyrosine phosphorylation of PIPKIγ661, but not PIPKIγ635, indicating that focal adhesion targeting was required for tyrosine phosphorylation of PIPKIγ661. Tyrosine phosphorylation of PIPKIγ661kd was also stimulated by co-expression of CD2FAK, although to a lesser extent. Co-expression of the dominant-negative FAK related non-kinase (FRNK), which blocks endogenous FAK activity, diminished tyrosine phosphorylation of PIPKIγ661. FRNK also inhibited adhesion-stimulated PIPKIγ661 tyrosine phosphorylation. The FAK-induced tyrosine phosphorylation of PIPKIγ661 correlated with a substantial increase in its association with talin. Tyrosine phosphorylation of PIPKIγ661 may facilitate association with talin via the phosphotyrosine-binding site in the talin head (Calderwood, et al. (2002) supra). Significantly, CD2FAK, but not FRNK, specifically stimulated the activity of PIPKIγ661. These data indicate that FAK signaling stimulates both talin association and PIP kinase activity, resulting in localized generation of PtdIns(4,5)P$_2$ at focal adhesions.

A functional link between PIPKIγ661 and FAK was provided by the observation that PIPKIγ661kd, but not PIPKIγ661, disrupted targeting of FAK to focal adhesions. PIPKIγ661 and PIPKIγ661kd were both targeted to focal adhesions and co-localized with FAK. High expression of PIPKIγ661 did not affect FAK targeting. In contrast, the expression of PIPKIγ661kd resulted in complete loss of FAK targeting to focal adhesions in 39% of the expressing cells. A number of other focal adhesion proteins were analyzed to determine the effect of PIPKIγ661 and PIPKI661γkd expression. From these studies, paxillin and vinculin were more resistant to changes induced by ectopic expression of PIPKIγ661 or PIPKI661γkd.

Further, PIPKIγ661 tyrosine phosphorylation stimulation by FAK was dependent upon both FAK phosphorylation on Tyr$^{397}$ and FAK activity, since neither co-expressed Tyr$^{397}$->Phe or kinase dead mutants of FAK induced phosphorylation of PIPKIγ661. To narrow the phosphorylation sites of PIPKIγ661, the PIPKIα/γ chimeras were co-expressed with wild-type FAK in HEK293T cells, and tyrosine phosphorylation of these proteins was analyzed. Both PIPKIα/γ661 and PIPKIα/γ26 were phosphorylated by FAK, but not PIPKIα/γ635, indicating that the major FAK signaling phosphorylation sites were in the last 26 amino acids of PIPKIγ661. In parallel, tail-truncation mutants of PIPKIγ661 were constructed (FIG. 3) and the ability of the mutants to be phosphorylated by co-expressed FAK was examined. PIPKIγ-W, which lacked both Tyr$^{644}$ and Tyr$^{649}$, was not phosphorylated while PIPKIγ-Y containing Tyr$^{644}$ was phosphorylated, but to a lesser extent. PIPKIγ-E retained both Tyr$^{644}$ and Tyr$^{649}$ and was phosphorylated similar to the wild-type kinase. This indicated that Tyr$^{644}$ and Tyr$^{649}$ were potential FAK signaling phosphorylation sites. Further, Tyr to Phe point mutants at positions 644 and 649 of PIPKIγ661 were constructed and tyrosine phosphorylation was assayed in cells. PIPKIγTyr$^{649}$->Phe was still phosphorylated by FAK at the levels similar to wild-type PIPKIγ661. However, PIPKIγTyr$^{644}$->Phe showed a dramatic reduction in phosphorylation, indicating that Tyr$^{644}$ was the FAK signaling phosphorylation site. These data, combined with the weak phosphorylation of PIPKIγ-Y indicated that the residues from Ser$^{645}$ to Glu$^{658}$ were required for efficient phosphorylation of PIPKIγ661.

In the FAK signaling pathway, Src family tyrosine kinases bind to and are activated by FAK, playing a fundamental role in focal adhesion organization (Parsons, et al. (2000) *Oncogene* 19:5606-5613; Cobb, et al. (1994) *Mol. Cell. Biol.* 14:147-155; Schaller, et al. (1994) *Mol. Cell. Biol.* 14:1680-1688; Schaller, et al. (1999) *Mol. Cell. Biol.* 10:3489-3505). To determine if Src family kinases phosphorylate PIPKIγ661, Src-specific inhibitor PP2 was employed. It was found that PP2, but not the inactive analogue PP3, dramatically inhibited both basal and FAK-induced tyrosine phosphorylation of PIPKIγ661, indicating that Src family kinases phosphorylated PIPKIγ661. Furthermore, the results from in vitro kinase assays demonstrated that c-Src directly phosphorylated recombinant PIPKIγ661 tail, while FAK does not. Consistent with these results, both recombinant PIPKIγTyr$^{644}$->Phe and PIPKIγTyr$^{644/649}$->Phe were not efficiently phosphorylated by c-Src in vitro compared with wild-type. PIPKIγTyr$^{649}$->Phe is efficiently phosphorylated by c-Src. These results demonstrate that Tyr$^{644}$ of PIPKIγ661 is the direct phosphorylation site of c-Src. Two-dimensional phosphopeptide mapping indicated that both Tyr$^{644}$ and Tyr$^{649}$ were phosphorylated by c-Src indicating that the phosphorylation of Tyr$^{649}$ may be depend upon the phosphorylation of Tyr$^{644}$.

The mechanism of PIPKIγ661 phosphorylation by Src was analyzed to determine whether there was an interaction between Src and PIPKIγ661. It was found that c-Src co-immunoprecipitated with PIPKIγ661. It has been shown that Src binding to FAK activates Src and both phosphorylate substrates synergistically (Schaller (2001) *Biochim. Biophys. Acta* 1540:1-21). The role of FAK in mediating Src phosphorylation of PIPKIγ661 was further examined. Co-expression of FAK and c-Src with PIPKIγ661 enhanced tyrosine phosphorylation and Src association with PIPKIγ661. Co-expression of FAK-Tyr$^{397}$->Phe lacking the docking site for Src interaction inhibited the association of PIPKIγ661 and c-Src. PIPKIγ635 and the PIPKIγ661 Tyr to Phe mutants could bind c-Src, indicating that c-Src interacts with PIPKIγ at a site distinct from the last 26 amino acids of PIPKIγ661 and independent of Tyr$^{644}$ or Tyr$^{649}$ phosphorylation. Since FAK does not interact with PIPKIγ661, these results indicate that FAK recruits c-Src to PIPKIγ661 by binding to the FERM domain of talin. This is further supported by the poor phosphorylation and weak talin interaction of PIPKIγ-Y although it contains Tyr$^{644}$.

Tyrosine phosphorylation of focal adhesion proteins regulates focal adhesion assembly by creating protein-protein interaction sites (Ridley and Hall (1994) *EMBO J.* 13:2600-2610; Chrzanowska-Wodnicka and Burridge (1994) *J. Cell Sci.* 107:3643-3654; Barry and Critchley (1994) *J. Cell Sci.* 107:2033-2045). As shown herein, increased PIPKIγ661 tyrosine phosphorylation by FAK signaling was correlated with PIPKIγ661/talin interaction. Talins interaction with PIPKIγ661 phosphorylation-defective mutants was analyzed to define whether PIPKIγ661 tyrosine phosphorylation was necessary for the interaction with talin. Compared with wild-type PIPKIγ661, PIPKIγ-W did not interact with talin, PIPKIγ-Y maintained weak talin association, and PIPKIγ-E had identical talin association. The tyrosine point mutants, PIPKIγTyr$^{644}$->Phe and PIPKIγTyr$^{644/649}$->Phe both showed substantially diminished talin association, while PIPKIγTyr$^{649}$->Phe retained talin association.

Targeting requirements were further examined by analyzing the focal adhesion localization of PIPKIγ661 mutants in NRK cells. PIPKIγ-W lost focal adhesion targeting, PIPKIγ-E targeted to focal adhesions and co-localized with talin similar to wild-type PIPKIγ661. PIPKIγ-Y partially retained focal adhesion targeting. Mutants lacking phosphorylation had reduced talin association and lost focal adhesion targeting, while PIPKIγTyr$^{649}$->Phe localized to focal adhesions similar to wild-type. Quantification revealed a correlation between focal adhesion targeting, talin association, and phosphorylation of PIPKIγ661.

Talin plays a key role in integrin-mediated signaling processes by linking integrins to the actin cytoskeleton and regulating integrin activation (Liu, et al. (2000) *J. Cell Sci.* 113:3563-3571; Calderwood, et al. (2002) *J. Biol. Chem.* 277:21749-21758). The F3 lobe of the talin FERM domain, structurally homologous to a phosphotyrosine binding-like (PTB-like) domain, binds to the β-integrin cytoplasmic tail (Calderwood, et al. (2002) supra; Garcia-Alvarez, et al. (2003) *Mol. Cell.* 11:49-58). As demonstrated herein, this region also binds the last 26 amino acids of PIPKIγ661. Accordingly, it was determined whether PIPKIγ661 tyrosine phosphorylation directly enhanced its interaction with talin. In addition, it was examined whether PIPKIγ661 would displace β-integrin from talin in a phosphorylation dependent manner.

Talin interactions were assessed by GST pull-down using recombinant GST-talin head, His-PIPKIγ635 C-terminus, His-PIPKIγ661 wild-type or Tyr to Phe mutant C-terminus, and His-β1-integrin tail. His-PIPKIγ661 Tyr to Phe mutants showed identical binding to talin compared to wild-type, indicating that the decreased in vivo talin association directly resulted from the lack of phosphorylation. Furthermore, it was found that His-PIPKIγ661, but not His-PIPKIγ635, competed with His-β1-integrin for binding to GST-talin in a dose-dependent manner. Peptides containing the PIPKIγ661/talin binding sequence (Di Paolo, et al. (2002) supra) were designed to include phosphorylated Tyr$^{644}$, phosphorylated Tyr$^{649}$, and dual phosphorylated Tyr$^{644}$ and Tyr$^{649}$. The phosphorylated peptides displaced PIPKIγ661 from talin more efficiently than the non-phosphorylated peptide in HEK293T cell lysates. In vitro, the non-phosphorylated peptide poorly displaced His-β1-integrin from GST-talin, while the phosphorylated peptides competed with a 20-fold higher affinity.

From structural studies of integrin binding to talin, a conserved tryptophan in β-integrin tail is positioned near two basic residues, Lys$^{357}$ and Arg$^{358}$ of talin F3 lobe (Garcia-Alvarez, et al. (2003) supra). It was demonstrated that Trp642 of PIPKIγ661 is a key residue required for talin binding (Di Paolo, et al. (2002) supra), positioning the Tyr644 adjacent to Lys357 and Arg$^{358}$ of talin. To determine if the binding affinity of the phosphorylated peptides was due to these two basic residues, each was mutated to glutamine. Both Lys$^{357}$->Gln and Arg$^{358}$->Gln mutants abolished His-β1-integrin binding, but unexpectedly, had no effect on His-PIPKIγ661 binding. These data demonstrate that PIPKIγ661 binds to talin on an overlapping yet distinct site compared to β1-integrin. The role of PIPKIγ661 phosphorylation was examined by using phosphorylated peptides to compete His-PIPKIγ661 binding to wild-type or mutant GST-talin. It was found that Lys$^{357}$->Gln retained high affinity binding for the Tyr$^{644}$-phosphorylated peptide but lower affinity for the Tyr$^{649}$-phosphorylated peptide. Arg$^{358}$->Gln showed a loss of affinity for both Tyr$^{644}$-and Tyr$^{649}$- phosphorylated peptides. This indicated that both phosphorylated residues require Arg$^{358}$->Gln for high affinity binding but the Tyr$^{649}$ appears to also require Lys$^{357}$->Gln. The enhanced association of the phosphorylated peptides with talin indicated that the β1-integrin tail may bind to talin with increased affinity when phosphorylated at the $^{780}$Trp-Asp-Thr$^{783}$ and $^{785}$Asn-Pro-Ile-Tyr$^{788}$(SEQ ID NO:1) motif, since the Trp-Asp-Thr aligns with Tyr$^{644}$ of PIPKIγ661. Accordingly, Arg$^{358}$->Gln would coordinate the phosphorylated Thr similar to Tyr$^{644}$ of PIPKIγ661. To further analyze this, β1-integrin peptides phosphorylated at Thr of Trp-Asp-Thr and at Tyr of Asn-Pro-Ile-Tyr (SEQ ID NO:1) were synthesized and used to compete integrin tail binding from talin. The phosphorylated Trp-Asp-Thr peptide did not increase binding affinity to talin. However, the phosphorylated Asn-Pro-Ile-Tyr (SEQ ID NO:1) peptide showed lower binding affinity, indicating that phosphorylation of the Tyr residue poorly interacted with GST-talin, consistent with previous reports (Garcia-Alvarez, et al. (2003) supra; Barsukov, et al. (2003) *J. Biol. Chem.* M303850200).

The interaction between talin and Src-phosphorylated PIPKIγ661 was further analyzed by computer modeling the talin F3 lobe (Garcia-Alverez, et al. (2003) supra) with the dual phosphorylated PIPKIγ661 peptide. In this model, Tyr$^{644}$ of PIPKIγ661 is positioned to interact with Lys$^{357}$ and Arg$^{358}$ of talin. Unlike the integrin sequence, Pro$^{646}$ of PIPKIγ661 created a turn that positioned Tyr$^{649}$ directly adjacent to Lys$^{357}$ of talin. This is consistent with results provided herein that showed that the Lys$^{357}$->Gln mutant lost the enhanced binding to Tyr$^{649}$-phosphorylated peptide. As Lys$^{357}$ and Arg$^{358}$ of talin are key residues for binding phosphorylated Tyr$^{644}$ and Tyr$^{649}$ of PIPKIγ661, it was determined if Arg or Lys residues are conserved in other FERM domains. The Lys or Arg residues were found at the same position in other FERM domains including Moesin, Radixin, Ezrin, and Band 4.1 (Garcia-Alverez, et al. (2003) supra), indicating structurally conserved binding between FERM domains and phosphorylated tyrosine residues.

The interaction between PIPKIγ661 and talin appeared to be critical for focal adhesion assembly. This is supported by observations that a β-integrin binding site regulated by PtdIns(4,5)P$_2$ is located in the head region of talin within the FERM domain (Martel, et al. (2001) supra; Calderwood, et al. (1999) supra; Rees, et al. (1990) supra; Chisti, et al. (1998) supra). Proteins containing the FERM domain, such as protein 4.1 and talin, interact with integral membrane proteins, such as glycophorin or integrins, and these interactions are modulated by PtdIns(4,5)P$_2$ (Martel, et al. (2001) supra; Chisti, et al. (1998) supra; Anderson and Marchesi (1985) *Nature* 318:295-298; Hirao, et al. (1996) *J. Cell Biol.* 135:37-51). Therefore, the PIPKIγ661-talin interaction may be important in the initiation of focal adhesion assembly via regulation of integrin binding and other focal adhesion proteins by PtdIns(4, 5)P$_2$ (Critchley (2000) supra; Burridge and Chrzanowska-Wodnicka (1996) supra; Schwartz and Ginsberg (2002) supra; Gilmore and Burridge (1996) supra; Steimle, et al. (1999) supra; Martel, et al. (2001) supra).

While not wishing to be bound by any one mechanism of action, it is believed that upon clustering of integrins, talin and PIPKIγ661 are recruited to focal adhesions, inducing synthesis of PtdIns(4,5)P$_2$. Spatial generation of PtdIns(4, 5)P$_2$ facilitates the recruitment and regulation of proteins such as vinculin, α-actinin and FAK. The formation of a complex consisting of PIPKIγ661, talin, FAK, and Src, may facilitate Src interaction with PIPKIγ661 and phosphorylate PIPKIγ661 at Tyr$^{644}$. Tyrosine-phosphorylation of PIPKIγ661 increases binding affinity to talin and displaces β-integrin. Thus, regulated and localized generation of PtdIns(4,5)P$_2$ facilitates the assembly and/or disassembly of focal adhesions. PIPKI activity is also regulated by small G proteins (McNamee, et al. (1993) supra; Chong, et al. (1994) supra; Honda, et al. (1999) *Cell* 99:521-532) and by phosphatidic acid, a product of phospholipase D (PLD) (Jenkins, et al. (1994) *J. Biol. Chem.* 269:11547-11554). PLD activity is required for actin stress fiber formation and α-actinin assembly at focal adhesions (Kam and Exton (2001) *Mol. Cell Biol.* 21:4055-4066). In many cells, adhesion is essential for survival and growth, which require phosphoinositol 3-kinase (PI3K) activity (Cary and Guan (1999) supra). PI3K is also modulated by FAK, and may be dependent upon PIPKIγ661 for its substrate. Consequently, generation of PtdIns(4,5)P$_2$ by PIPKIγ661 may also control the generation of messengers derived from PtdIns(4,5)P$_2$. Thus, PIPKIγ661 may be at a signaling branch point that modulates both focal adhesion assembly and signals emanating from focal adhesions. As PIPKIγ661 appears to be central to focal adhesion assembly, agents which modulate the activity of PIPKIγ661 or events leading up to the phosphorylation of PIPKIγ661 (i.e., FAK and Src interactions) would be useful as therapeutics for cell-migration mediated conditions or diseases.

Accordingly, one aspect of the present invention is a method for identifying an agent that modulates the activity of PIPKIγ661. The method involves contacting PIPKIγ661 with a test agent in the presence of at least one selected protein and detecting the activity of PIPKIγ661, wherein a change in the activity of PIPKIγ661 compared to a control is indicative of the agent modulating the activity of PIPKIγ661. In one embodiment of the present invention, the activity of PIPKIγ661 is defined by the binding interaction with talin. In this embodiment, the selected protein is talin. In another embodiment the activity of PIPKIγ661 is defined by the phosphorylation of PIPKIγ661 in the presence of the selected protein Src. Further, the phosphorylation of PIPKIγ661 may be determined in the presence of Src in combination with FAK. As used herein, an agent which modulates the activity of PIPKIγ661 includes an agent which stimulates, enhances or activates its activity as well as an agent which inhibits, reduces or decreases the activity of PIPKIγ661. It is contemplated that an agent, which modulates the activity of PIPKIγ661 may interact with either PIPKIγ661 or talin to modulate the interaction between PIPKIγ661 and talin or interact with PIPKIγ661, Src or FAK to modulate the phosphorylation of PIPKIγ661. An agent with interacts with Src or FAK modulates the activity of Src or FAK thereby modulating the activity of PIPKIγ661.

A PIPKIγ661 protein which may be used within the scope of the invention includes a full-length PIPKIγ661 (SEQ ID NO:2) or any fragment, homolog, or ortholog which binds to talin. In a preferred embodiment of the invention, a fragment of PIPKIγ661 encompasses the C-terminal 178 amino acid fragment of PIPKIγ661 (SEQ ID NO:3), the 25 C-terminal amino acid residues of PIPKIγ661 (Thr-Asp-Glu-Arg-Ser-Trp-Val-Tyr-Ser-Pro-Leu-His-Tyr-Ser-Ala-Arg-Pro-Ala-Ser-Asp-Gly-Glu-Ser-Asp-Thr; SEQ ID NO:4) or a fragment thereof (e.g., Asp-Glu-Arg-Ser-Trp-Val-Tyr-Ser-Pro-Leu-His-Tyr-Ser-Ala-Arg; SEQ ID NO:5).

When detecting the binding of PIPKIγ661 to talin, a talin protein which may be used within the scope of the invention includes a full-length talin (SEQ ID NO:6) or any fragment which binds to PIPKIγ661. In a preferred embodiment of the invention, a fragment of talin encompasses the 450 N-terminal amino acid residues of talin (SEQ ID NO:7), residues 150-450 of talin (SEQ ID NO:8) which bind PIPKIγ661 or residues 206-435 of talin (SEQ ID NO:9) which bind β-integrin.

When detecting the phosphorylation of PIPKIγ661 by Src, a Src protein which may be used includes a full-length Src (SEQ ID NO:10) or any fragment which phosphorylates PIPKIγ661. Further, when the assay is carried out in the presence of FAK, a FAK protein may include a full-length FAK (SEQ ID NO:11) or any fragment which modulates the phosphorylation of PIPKIγ661 via Src.

A PIPKIγ661, Src, FAK or talin protein or fragment thereof may be derived from the native polypeptide sequence, as well as recombinantly-produced or chemically-synthesized polypeptides which function in a manner similar to the reference molecule to achieve a desired result. Thus, a functional fragment of PIPKIγ661, Src, FAK or talin encompasses derivatives, homologues, orthologs and analogues of those polypeptides including any single or multiple amino acid additions, substitutions, and/or deletions occurring internally or at the amino or carboxy termini thereof so long as binding activity remains.

Methods for producing recombinant PIPKIγ661, Src, FAK or talin proteins are well-known in the art. In general, nucleic acid sequences encoding PIPKIγ661, Src, FAK or talin are incorporated into a recombinant expression vector in a form suitable for expression of the proteins in a host cell. A suitable form for expression provides that the recombinant expression vector includes one or more regulatory sequences operatively-linked to the nucleic acids encoding PIPKIγ661, Src, FAK or talin in a manner which allows for transcription of the nucleic acids into mRNA and translation of the mRNA into the protein. Regulatory sequences may include promoters, enhancers and other expression control elements (e.g., polyadenylation signals). Such regulatory sequences are known to those skilled in the art and are described in Goeddel D. D., ed., Gene Expression Technology, Academic Press, San Diego, Calif. (1991). It should be understood that the design of the expression vector may depend on such factors as the choice of the host cell to be transfected and/or the level of expression required.

A PIPKIγ661, Src, FAK or talin protein may be expressed not only directly, but also as a fusion protein with a heterologous polypeptide, i.e. a signal sequence for secretion and/or other polypeptide which will aid in the purification of PIPKIγ661, Src, FAK or talin. Preferably, the heterologous polypeptide has a specific cleavage site to remove the heterologous polypeptide from PIPKIγ661, Src, FAK or talin.

In general, a signal sequence may be a component of the vector and should be one that is recognized and processed (i.e., cleaved by a signal peptidase) by the host cell. For production in a prokaryote, a prokaryotic signal sequence from, for example, alkaline phosphatase, penicillinase, lpp, or heat-stable enterotoxin II leaders may be used. For yeast secretion, one may use, e.g., the yeast invertase, alpha factor, acid phosphatase leaders, the *Candida albicans* glucoamylase leader (EP 362,179), or the like (see, for example WO 90/13646). In mammalian cell expression, signal sequences from secreted polypeptides of the same or related species, as well as viral secretory leaders, for example, the herpes simplex glycoprotein D signal may be used.

Other useful heterologous polypeptides which may be fused to PIPKIγ661, Src, FAK or talin include those which increase expression or solubility of the fusion protein or aid in the purification of the fusion protein by acting as a ligand in affinity purification. Typical fusion expression vectors include those exemplified herein (fusion vectors of c-Myc and HA) as well as pGEX vectors (Amersham Biosciences, Piscataway, N.J.), pMAL and pTYB vectors (New England Biolabs, Beverly, Mass.) and pRIT5 (Pharmacia Biotech, Piscataway, N.J.) which fuse glutathione-S-transferase, maltose E binding protein, intein/chitin binding domain or protein A, respectively, to the target recombinant protein.

PIPKIγ661, Src, FAK or talin is expressed in a cell by introducing nucleic acid sequences encoding PIPKIγ661, Src, FAK or talin into a host cell, wherein the nucleic acids are in a form suitable for expression of PIPKIγ661, Src, FAK or talin in the host cell. Alternatively, nucleic acid sequences encoding PIPKIγ661, Src, FAK or talin which are operatively-linked to regulatory sequences (e.g., promoter sequences) but without additional vector sequences may be introduced into a host cell. As used herein, a host cell is intended to include any prokaryotic or eukaryotic cell or cell line so long as the cell or cell line is not incompatible with the protein to be expressed, the selection system chosen or the fermentation system employed.

Eukaryotic cell or cell lines which may be used to produce PIPKIγ661, Src, FAK or talin include mammalian cell lines as well as non-mammalian cells. Exemplary mammalian cell lines include, but are not limited to, those exemplified herein as well as CHO dhfr-cells (Urlaub and Chasin (1980) *Proc. Natl. Acad. Sci. USA* 77:4216-4220), 293 cells (Graham, et al. (1977) *J. Gen. Virol.* 36:59) or myeloma cells like SP2 or NSO (Galfre and Milstein (1981) *Meth. Enzymol.* 73(B):3-46). A variety of non-mammalian eukaryotic cells may be used as well, including insect (e.g,. *Spodoptera frugiperda*), yeast (e.g., *S. cerevisiae, Schizosaccharomyces pombe, Pichia pastoris, Kluveromyces lactis, Hansenula polymorpha,* and *Candida albicans*), fungal cells (e.g., *Neurospora crassa, Aspergillus nidulins, Aspergillus fumigatus*) and plant cells.

While any prokaryotic cell may be used to produce PIPKIγ661, Src, FAK or talin, *Escherichia coli* is the most common prokaryotic expression system. Strains which may be used to maintain expression plasmids include, but are not limited to, JM103, JM105, and JM107. Exemplary *E. coli* strains for protein production include W3110 (ATCC 27325), *E. coli* B, *E. coli* X1776 (ATCC 31537), *E. coli* BL21 (Amersham Biosciences, Piscataway, N.J.), *E. coli* ER5266 (New England Biolabs, Beverly, Mass.) and *E. coli* 294 (ATCC 31446).

For production of PIPKIγ661, Src, FAK or talin in recombinant prokaryotic expression vectors it is contemplated that protein expression may be regulated by promoters such as the beta-lactamase (penicillinase) and lactose promoter systems (Chang, et al. (1978) *Nature* 275:615; Goeddel, et al. (1979) *Nature* 281:544), a tryptophan (trp) promoter system (Goeddel, et al. (1980) *Nucl. Acids Res.* 8:4057; EP 36,776) the tac promoter (De Boer, et al. (1983) *Proc. Natl. Acad. Sci. USA* 80:21) or pL of bacteriophage 1. These promoters and Shine-Dalgarno sequence may be used for efficient expression of PIPKIγ661, Src, FAK or talin in prokaryotes.

Eukaryotic microbes such as yeast may be transformed with suitable vectors containing nucleic acids encoding PIPKIγ661, Src, FAK or talin. *Saccharomyces cerevisiae* is the most commonly studied lower eukaryotic host microorganism, although a number of other species already mentioned are commonly available. Yeast vectors may contain an origin of replication from the 2 micron yeast plasmid or an autonomously replicating sequence (ARS), a promoter, nucleic acid sequences encoding PIPKIγ661, Src, FAK or talin, sequences for polyadenylation and transcription termination, and nucleic acid sequences encoding a selectable marker. Exemplary plasmids include YRp7 (Stinchcomb, et al. (1979) *Nature* 282:39; Kingsman, et al. (1979) *Gene* 7:141; Tschemper, et al. (1980) *Gene* 10:157), pYepSec1 (Baldari, et al. (1987) *EMBO J.* 6:229-234), pMFa (Kurjan and Herskowitz (1982) *Cell* 30:933-943), pJRY88 (Schultz, et al. (1987) *Gene* 54:113-123), and pYES2 (INVITROGEN™ Corporation, San Diego, Calif.). These plasmids contain genes such as trp1, which provides a selectable marker for a mutant strain of yeast lacking the ability to grow in the presence of tryptophan, for example ATCC No. 44076 or PEP4-1 (Jones (1977) *Genetics* 85:12). The presence of the trp1 lesion in the yeast host cell genome then provides an effective environment for detecting transformation by growth in the absence of tryptophan.

Suitable sequences for promoting PIPKIγ661, Src, FAK or talin expression in yeast vectors include the promoters for metallothionein, 3-phosphoglycerate kinase (Hitzeman, et al. (1980) *J. Biol. Chem.* 255:2073) or other glycolytic enzymes (Hess, et al. (1968) *J. Adv. Enzyme Reg.* 7:149; Holland, et al. (1978) *Biochemistry* 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further disclosed in EP 73,657.

When the host cell is from an insect (e.g., *Spodoptera frugiperda* cells), expression vectors such as the baculovirus expression vector (e.g., vectors derived from *Autographa californica* MNPV, *Trichoplusia ni* MNPV, *Rachiplusia ou* MNPV, or *Galleria ou* MNPV, as described in U.S. Pat. Nos. 4,745,051 and 4,879,236) may be employed to express PIPKIγ661, Src, FAK or talin. In general, a baculovirus expression vector comprises a baculovirus genome containing nucleic acid sequences encoding PIPKIγ661, Src, FAK or talin inserted into the polyhedrin gene at a position ranging from the polyhedrin transcriptional start signal to the ATG start site and under the transcriptional control of a baculovirus polyhedrin promoter.

In plant cells, expression systems are often derived from recombinant Ti and Ri plasmid vector systems. In the cointegrate class of shuttle vectors, the gene of interest is inserted by genetic recombination into a non-oncogenic Ti plasmid that contains both the cis-acting and transacting elements required for plant transformation. Exemplary vectors include the pMLJ1 shuttle vector (DeBlock, et al. (1984) *EMBO J.* 3:1681-1689) and the non-oncogenic Ti plasmid pGV2850 (Zambryski, et al. (1983) *EMBO J.* 2:2143-2150). In the binary system, the gene of interest is inserted into a shuttle vector containing the cis-acting elements required for plant transformation. The other necessary functions are provided in trans by the non-oncogenic Ti plasmid. Exemplary vectors include the pBIN19 shuttle vector (Bevan (1984) *Nucl. Acids Res.* 12:8711-8721) and the non-oncogenic Ti plasmid pAL4404 (Hoekema, et al. (1983) *Nature* 303:179-180) and derivatives thereof.

Promoters used in plant expression systems are typically derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV).

In mammalian cells the recombinant expression vector may be a plasmid. Alternatively, a recombinant expression vector may be a virus, or a portion thereof, which allows for expression of a nucleic acid introduced into the viral nucleic acid. For example, replication-defective retroviruses, adenoviruses and adeno-associated viruses may be used. Protocols for producing recombinant retroviruses and for infecting cells in vitro or in vivo with such viruses may be found in Current Protocols in Molecular Biology, Ausubel, F. M. et al. (eds.) John Wiley & Sons, (1996), Section 9 and other standard laboratory manuals. Examples of suitable retroviruses include, but are not limited to, pLJ, pZIP, pWE and pEM which are well-known to those skilled in the art. Examples of suitable packaging virus lines include, but are not limited to, ψCrip, ψCre, ψ2 and ψAm. The genome of adenovirus may be manipulated such that it encodes and expresses PIPKIγ661 or talin but is inactivated in terms of its ability to replicate in a normal lytic viral life cycle (Berkner, et al. (1988) *BioTechniques* 6:616; Rosenfeld, et al. (1991) *Science* 252:431-434; Rosenfeld, et al. (1992) *Cell* 68:143-155). Suitable adenoviral vectors derived from the adenovirus strain Ad type 5 d1324 or other strains of adenovirus (e.g., Ad2, Ad3, Ad7 etc.) are well-known to those skilled in the art. Alternatively, an adeno-associated virus vector such as that taught by Tratschin, et al. ((1985) *Mol. Cell. Biol.* 5:3251-3260) may be used to express PIPKIγ661, Src, FAK or talin.

In mammalian expression systems, the regulatory sequences are often provided by the viral genome. Commonly used promoters are derived from polyoma, Adenovirus 2, cytomegalovirus and Simian Virus 40. For example, the human cytomegalovirus IE promoter (Boshart, et al. (1985) *Cell* 41:521-530), HSV-Tk promoter (McKnight, et al. (1984) *Cell* 37:253-262) and β-actin promoter (Ng, et al. (1985) *Mol. Cell. Biol.* 5:2720-2732) may be useful in the expression of PIPKIγ661, Src, FAK or talin in mammalian cells. Alternatively, the regulatory sequences of the recombinant expression vector may direct expression of PIPKIγ661, Src, FAK or talin preferentially in a particular cell-type, i.e., tissue-specific regulatory elements may be used. Examples of tissue-specific promoters which may be used include, but are not limited to, the albumin promoter (liver-specific; Pinkert, et al. (1987) *Genes Dev.* 1:268-277), lymphoid-specific promoters (Calame and Eaton (1988) *Adv. Immunol.* 43:235-275), promoters of T cell receptors (Winoto and Baltimore (1989) *EMBO J.* 8:729-733) and immunoglobulins (Banerji, et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci USA* 86:5473-5477), pancreas-specific promoters (Edlund, et al. (1985) *Science* 230:912-916), and mammary gland-specific promoters (e.g., milk whey promoter; U.S. Pat. No. 4,873,316; EP 264,166). Developmentally-regulated promoters are also encompassed, for example the murine hox promoters (Kessel and Gruss (1990) *Science* 249:374-379) and the α-fetoprotein promoter (Camper and Tilghman (1989) *Genes Dev.* 3:537-546).

Nucleic acid sequences or expression vectors harboring nucleic acid sequences encoding PIPKIγ661, Src, FAK or talin may be introduced into a host cell by standard techniques for transforming cells. Transformation or transfection are intended to encompass all conventional techniques for introducing nucleic acid into host cells, including calcium phosphate co-precipitation, DEAE-dextran-mediated transfection, lipofection, electroporation, microinjection, polyethylene glycol-mediated transformation, viral infection, *Agrobacterium*-mediated transformation, cell fusion, and ballistic bombardment. Suitable methods for transforming host cells may be found in Sambrook, et al. (Molecular Cloning: A Laboratory Manual, 3rd Edition, Cold Spring Harbor Laboratory Press (2000)) and other laboratory manuals.

The number of host cells transformed with a nucleic acid sequence encoding PIPKIγ661, Src, FAK or talin will depend, at least in part, upon the type of recombinant expression vector used and the type of transformation technique used. Nucleic acids may be introduced into a host cell transiently, or more typically, for long-term expression of PIPKIγ661, Src, FAK or talin, the nucleic acid sequence is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is generally introduced into the host cells along with the nucleic acids of interest. Preferred selectable markers include those which confer resistance to certain drugs, such as G418 and hygromycin. Selectable markers may be introduced on a separate plasmid from the nucleic acids of interest or introduced on the same plasmid. Host cells transfected with nucleic acid sequences encoding PIPKIγ661, Src, FAK or talin (e.g., a recombinant expression vector) and a gene for a selectable marker may be identified by selecting for cells using the selectable marker. For example, if the selectable marker encodes a gene conferring neomycin resistance, host cells which have taken up the nucleic acid sequences of interest may be selected with G418 resistance. Cells that have incorporated the selectable marker gene will survive, while the other cells die.

A host cell transformed with nucleic acid sequences encoding PIPKIγ661, Src, FAK or talin may be used for expressing PIPKIγ661, Src, FAK or talin for protein production or may be used in cell-based screening assays to identify agents which modulate cell adhesion. Further, a host cell transformed with nucleic acid sequences encoding PIPKIγ661, Src, FAK or talin may be transformed with one or more nucleic acid sequences which serve as targets for PIPKIγ661, Src, FAK or talin.

Nucleic acid sequences encoding PIPKIγ661, Src, FAK or talin may be introduced into cells growing in culture in vitro by conventional transformation techniques (e.g., calcium phosphate precipitation, DEAE-dextran transfection, electroporation, etc.). Nucleic acids may also be transferred into cells in vivo, for example by application of a delivery mechanism suitable for introduction of nucleic acid into cells in vivo, such as retroviral vectors (see e.g., Ferry, et al. (1991) *Proc. Natl. Acad. Sci. USA* 88:8377-8381; Kay, et al. (1992) *Hum. Gene Ther.* 3:641-647), adenoviral vectors (see e.g., Rosenfeld (1992) *Cell* 68:143-155; Herz and Gerard (1993) *Proc. Natl. Acad. Sci. USA* 90:2812-2816), receptor-mediated DNA uptake (see e.g., Wu and Wu (1988) *J. Biol. Chem.* 263:14621; Wilson, et al. (1992) *J. Biol. Chem.* 267:963-967; U.S. Pat. No. 5,166,320), direct injection of DNA uptake (see e.g., Acsadi, et al. (1991) *Nature* 334:815-818; Wolff, et al. (1990) *Science* 247:1465-1468) or particle bombardment (see e.g., Cheng, et al. (1993) *Proc. Natl. Acad. Sci. USA* 90:4455-4459; Zelenin, et al. (1993) *FEBS Let.* 315:29-32).

Nucleic acid sequences encoding PIPKIγ661, Src, FAK or talin may be transferred into a fertilized oocyte of a non-human animal to create a transgenic animal which expresses PIPKIγ661, Src, FAK or talin in one or more cell-types. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell-types or tissues of the transgenic animal. Exemplary examples of non-human animals include, but are not limited to, mice, goats, sheep, pigs, cows or other domestic farm animals. Such transgenic animals are useful, for example, for large-scale production of PIPKIγ661, Src, FAK or talin (gene pharming) or for basic research investigations.

A transgenic animal may be created, for example, by introducing a nucleic acid sequence encoding PIPKIγ661, Src, FAK or talin, typically linked to appropriate regulatory sequences, such as a constitutive or tissue-specific enhancer, into the male pronuclei of a fertilized oocyte, e.g., by microinjection, and allowing the oocyte to develop in a pseudopregnant female foster animal. Intron sequences and polyadenylation signals may also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009. A transgenic founder animal may be used to breed additional animals carrying the transgene. Transgenic animals carrying a transgene encoding PIPKIγ661, Src, FAK or talin may further be bred to other transgenic animals carrying other transgenes, e.g., a transgenic animal overexpressing PIPKIγ661 may be bred with a transgenic animal overexpressing talin.

Once produced, the PIPKIγ661, Src, FAK or talin may be recovered from culture medium or milk as a secreted polypeptide, although it also may be recovered from host cell lysates when directly expressed without a secretory signal. When PIPKIγ661, Src, FAK or talin is expressed in a recombinant cell other than one of human origin, the PIPKIγ661, Src, FAK or talin is free of proteins or polypeptides of human origin. However, it may be necessary to purify PIPKIγ661, Src, FAK or talin from recombinant cell proteins or polypeptides to obtain preparations that are substantially homogeneous as to PIPKIγ661, Src, FAK or talin. As a first step, the culture medium or lysate is centrifuged to remove particulate cell debris. The membrane and soluble protein fractions are then separated. The PIPKIγ661, Src, FAK or talin may then be purified from the soluble protein fraction. PIPKIγ661, Src, FAK or talin thereafter is purified from contaminant soluble proteins and polypeptides, as exemplified herein or with, for example, the following suitable purification procedures: by fractionation on immunoaffinity or ion-exchange columns; ethanol precipitation; chitin column chromatography, reverse phase HPLC; chromatography on silica or on a cation-exchange resin such as DEAE; chromatofocusing; SDS-PAGE; ammonium sulfate precipitation; gel filtration using, for example, SEPHADEX G-75; ligand affinity chromatography, and protein A SEPHAROSE columns to remove contaminants such as IgG.

In addition to recombinant production, PIPKIγ661, Src, FAK or talin or fragments thereof may be produced by direct peptide synthesis using solid-phase techniques (Merrifield J. (1963) *J. Am. Chem. Soc.* 85:2149-2154). Protein synthesis may be performed using manual techniques or by automation. Automated synthesis may be achieved, for example, using Applied Biosystems 431A Peptide Synthesizer (Perkin Elmer, Boston, Mass.). Various fragments of PIPKIγ661, Src, FAK or talin may be chemically-synthesized separately and combined using chemical methods to produce the full-length molecule.

Whether recombinantly-produced or chemically-synthesized, PIPKIγ661, Src, FAK or talin polypeptides or fragments thereof may be further modified for use in the screening methods of the invention. For example, the peptides or polypeptides may be glycosylated, phosphorylated or fluorescently-tagged using well-known methods. For example, Src may be phosphorylated prior to screening assays with PIPKIγ661.

Screening assays for identifying an agent which modulates the activity of PIPKIγ661 may be performed in any format that allows rapid preparation and processing of multiple reactions such as in, for example, multi-well plates of the 96-well variety. Stock solutions of the agents as well as assay components are prepared manually and all subsequent pipeting, diluting, mixing, washing, incubating, sample readout and data collecting is done using commercially available robotic pipeting equipment, automated work stations, and analytical instruments for detecting the signal generated by the assay.

In addition to PIPKIγ661 and Src/FAK or talin, a variety of other reagents may be included in the screening assays. These include reagents like salts, neutral proteins, e.g., albumin, detergents, etc. which may be used to facilitate optimal protein-protein binding and/or reduce non-specific or background interactions. Also, reagents that otherwise improve the efficiency of the assay, such as protease inhibitors, nuclease inhibitors, anti-microbial agents, and the like may be used. The mixture of components may be added in any order that provides for the requisite binding.

In a screening assay to identify an agent which modulates the activity of PIPKIγ661 as defined by the binding interaction between PIPKIγ661 and talin, the step of detecting the activity of PIPKIγ661 is carried out by detecting and measuring the binding of PIPKI-γ661 to talin. The detection and measurement of this binding interaction will be dependent on the type of screening assay performed and the labels used. Such screening assays to detect binding between two proteins in the presence of a test agent are well-known in the art. In a preferred embodiment of the present invention, a fluorescently labeled PIPKIγ661 peptide is used in a binding assay with talin or a fragment thereof to identify agents which modulate the PIPKIγ661 and talin interaction. An exemplary binding assay of this type was conducted using PIPKIγ661 peptides of the sequence Cys-Asp-Glu-Arg-Ser-Trp-Val-Tyr-Ser-Pro-Leu-His-Tyr-Ser-Ala-Arg (peptide designated PN; SEQ ID NO:12) which are encompassed within the C-terminal 25 amino acid residues of PIPKIγ661 and interact with talin at the same site as integrin. A cysteine residue at the N-terminus of the PIPKIγ661 peptides provides a residue which may be modified with a probe, preferably a fluorescent probe. Fluorescent probes may be linked to the cysteine residue using conventional thiol or thioester linkages. Upon binding to the N-terminal 450 amino acid residues of talin, a PIPKIγ661 peptide of SEQ ID NO:12 or derivatives thereof exhibited a large change in rotational motion as detected by changes in fluorescent emission anisotropy. It was found that peptides phosphorylated at tyrosines located at Tyr residue 644 (peptide designated pY644), Tyr residue 649 (peptide pY649) or Tyr residue 644 and 649 (peptide designated pY644/649) had a higher binding affinity for talin than did the unphosphorylated peptide (i.e., peptide PN) in a binding assay between talin and integrin (FIG. 2). In this assay, an agent which is an inhibitor of the interaction between PIPKIγ661 and talin blocks binding of a peptide of SEQ ID NO:12 and changes the fluorescent emission anisotropy as compared to a control (e.g., binding in the absence of the inhibitor).

When assaying test agents, a control may also include a known agent which has a high affinity for binding and inhibiting the interaction between PIPKIγ661 and talin (e.g., PIPKIγ661 peptides pY644, pY649, and pY644/649) or a known agent which has a low affinity for binding and inhibiting the interaction between PIPKIγ661 and talin (e.g., PIPKIγ661 peptide PN). An agent that modulates the level of bound PIPKIγ661 to talin is one which, for example, blocks binding of a PIPKIγ661 peptide of SEQ ID NO:12 and decreases the fluorescence emission anisotropy of said peptide.

Exemplary fluorescent probes which may be attached to the N-terminus of a PIPKIγ661 peptide are well-known in the art and include, but are not limited to, α-Phycoerythrin, Green Fluorescent Protein, Phycocyanine, Allophycocyanine, Tricolor, AMCA, AMCA-S, AMCA, BODIPY FL, BODIPY 493/503, BODIPY FL Br2, BODIPY R6G, BODIPY 530/550, BODIPY TMR, BODIPY 558/568, BODIPY 564/570, BODIPY 576/589, BODIPY 581/591, BODIPY TR, Cascade Blue, CI-NERF, Dansyl, Dialkylaminocoumarin, 4',6'-Dichloro-2',7'-dimethoxy-fluorescein, 2',7'-dichloro-fluorescein, Cy3, Cy5, Cy7, DM-NERF, Eosin, Eosin F3S, Erythrosin, Fluorescein, Fluorescein Isothiocyanate Hydroxycoumarin, Isosulfan Blue, Lissamine Rhodamine B, Malachite Green, Methoxycoumarin, Napthofluorecein, NBD, Oregon Green 488, Oregon Green 500, Oregon Green 514, Propidium Iodide Phycoerythrin, PyMPO, Pyrene, Rhodamine 6G, Rhodamine Green, Rhodamine Red, Rhodol Green, 2',4',5',7'-Tetrabromosulfonefluorescein, Tetramethyl-rhodamine, Texas Red, X-rhodamine; Lucifer Yellow and the like. Detection of changes in fluorescence may be carried out using such methods as fluorescence spectroscopy, fluorescence resonance energy transfer (FRET), fluorescent lifetime imaging (FLIM) (Lakowicz, et al. (1992) *Anal. Biochem.* 202:316-330), or fluorescence polarization.

As PIPKIγ661 and integrin have overlapping binding sites on talin, the ability of a test agent to modulate the binding between talin and integrin also may be assayed to identify the specificity of the agent that modulates the interaction between PIPKIγ661 and talin. In other words, it may be determined whether the agent binds to talin or PIPKIγ661 to modulate their interaction. Accordingly, an integrin which may be used includes a full-length integrin (SEQ ID NO:13) or any fragment which binds to talin (e.g., β1-integrin tail; Cys-Met-Asn-Ala-Lys-Trp-Asp-Thr-Gly-Glu-Asn-Pro-Ile-Tyr-Lys-Ser-Ala; SEQ ID NO:14).

In a screening assay for an agent which modulates the activity of PIPKIγ661 as determined by the phosphorylation of PIPKIγ661 in the presence of Src or Src and FAK, the step of detecting the activity of PIPKIγ661 is carried out by detecting the presence or absence of phosphorylation of PIPKIγ661. Preferably, the phosphorylation state of Tyr$^{644}$ of PIPKIγ661 is detected. The phosphorylation assay is carried out under suitable assay conditions using well-known methods and a phosphate donor may be added with or after the agent.

It is contemplated that the phosphorylation state of Tyr644 of PIPKIγ661 may be determined using a variety of separation and/or detection methods, including those exemplified herein. For example, [$^{32}$p] phosphorylated PIPKIγ661 is digested with trypsin and separated by well-known conventional column chromatography, 2-D gel electrophoresis, or capillary electrophoresis methodologies. For separation by column chromatography, reverse-phase HPLC may be employed with collection via peak detection. Under the conditions used for reverse-phase HPLC (0.05% TFA, pH 2.2), a phosphorylated peptide generally elutes slightly earlier than the corresponding non-phosphorylated peptide and may or may not be separated from it. Once HPLC fractions containing the phosphorylated Tyr$^{644}$ peptide of PIPKIγ661 are located by Cerenkov counting, a small aliquot of each may be analyzed by MALDI-MS.

As an alternative to radiolabeling, western blots made from 2-D gels may be probed using anti-phosphoserine antibodies (Research Diagnostics, Inc., Flanders, N.J.) to recognize the degree of phosphorylation of a peptide fragment of PIPKIγ661 containing Tyr$^{644}$.

Alternatively, one may use a phosphoprotein purification kit (QIAGEN®, Valencia, Calif.) for separation of the phosphorylated from the unphosphorylated cellular protein fraction. The affinity chromatography procedure, in which phosphorylated proteins are bound to a column while unphosphorylated proteins are recovered in the flow-through fraction, reduces complexity and greatly facilitates phosphorylation-profile studies. PIPKIγ661 may then be purified from each fraction and the degree of phosphorylation of PIPKIγ661 determined via autoradiography or immunoassays.

In a preferred embodiment, the phosphorylation of PIPKIγ661 is detected using an antibody which specifically recognizes the phosphorylation state of PIPKIγ661. Preferably, the antibody specifically recognizes the phosphorylation state of tyrosine residue 644 of PIPKIγ661.

An antibody which specifically recognizes the phosphorylation state of Tyr$^{644}$ may be either polyclonal or monoclonal so long as it is able to discriminate between the unphosphorylated and phosphorylated forms of Tyr$^{644}$ and bind PIPKIγ661 to form an PIPKIγ661-antibody complex, i.e., antigen-antibody complex. For example, an antibody which specifically recognizes the unphosphorylated state of Tyr$^{644}$ will only bind to an unphosphorylated Tyr$^{644}$ and not to a phosphorylated Tyr$^{644}$. Likewise, an antibody which specifically recognizes the phosphorylated state of Tyr$^{644}$ will only bind to a phosphorylated Tyr$^{644}$ and not to an unphosphorylated Tyr$^{644}$. In a preferred embodiment, the antibody recognizes the phosphorylated form of Tyr$^{644}$ of PIPKIγ661.

Antibodies which may be used to detect the phosphorylation state of Tyr644 may be natural or partially or wholly synthetically produced. All fragments or derivatives thereof which maintain the ability to specifically bind to and recognize the phosphorylation state of Tyr$^{644}$ are also contemplated. The antibodies may be a member of any immunoglobulin class, including any of the classes: IgG, IgM, IgA, IgD, and IgE. Derivatives of the IgG class, however, are preferred in the present invention.

Antibody fragments may be any derivative of an antibody which is less than full-length. Preferably, the antibody fragment retains at least a significant portion of the full-length antibody's specific binding ability. Examples of antibody fragments include, but are not limited to, Fab, Fab', F(ab')$_2$, scFv, Fv, dsFv diabody, or Fd fragments. The antibody fragment may be produced by any means. For instance, the antibody fragment may be enzymatically or chemically produced by fragmentation of an intact antibody or it may be recombinantly produced from a gene encoding the partial antibody sequence. The antibody fragment may optionally be a single-chain antibody fragment. Alternatively, the fragment may comprise multiple chains which are linked together, for instance, by disulfide linkages. The fragment may also optionally be a multi-molecular complex. A functional antibody fragment will typically comprise at least about 50 amino acids and more typically will comprise at least about 200 amino acids. As used herein, an antibody also includes bispecific and chimeric antibodies.

Naturally produced antibodies may be generated using well-known methods (see, e.g., Kohler and Milstein (1975) Nature 256:495-497; Harlow and Lane, In: Antibodies: A Laboratory Manual, Cold Spring Harbor Laboratory, New York (1988)). Alternatively, antibodies which specifically recognize the phosphorylation state of Tyr$^{644}$ are derived by a phage display method. Methods of producing phage display antibodies are well-known in the art (e.g., Huse, et al. (1989) Science 246(4935):1275-81).

Selection of PIPKIγ661-specific antibodies is based on binding affinity to Tyr$^{644}$ which is either phosphorylated or unphosphorylated and may be determined by the various well-known immunoassays provided herein.

In general, to detect the phosphorylation state of Tyr$^{644}$ using an antibody which specifically recognizes the phosphorylation state of Tyr644 involves detecting the formation of an antigen-antibody complex using an immunoassay. Any suitable immunoassay may be used in this method to detect and/or quantitate antigens. Exemplary immunoassays which may be used include, but are not limited to, enzyme-linked immunosorbent, immunodiffusion, chemiluminescent, immunofluorescent, immunohistochemical, radioimmunoassay, agglutination, complement fixation, immunoelectrophoresis, western blots, mass spectrometry, antibody array, and immunoprecipitation assays and the like which may be performed in vitro, in vivo or in situ. Such standard techniques are well-known to those of skill in the art (see, e.g., "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984) J. Clin. Chem. Clin. Biochem. 22:895-904; Harlow and Lane, Antibodies: A Laboratory Manual, Cold Spring Harbor Laboratory, New York (1988) 555-612).

These immunoassays typically rely on labeled antigens, antibodies, or secondary reagents for detection. These proteins may be labeled with radioactive compounds, enzymes, biotin, or fluorochromes. Of these, radioactive labeling may be used for almost all types of assays. Enzyme-conjugated labels are particularly useful when radioactivity must be avoided or when quick results are needed. Biotin-coupled reagents usually are detected with labeled streptavidin. Streptavidin binds tightly and quickly to biotin and may be labeled with radioisotopes or enzymes. Fluorochromes, although requiring expensive equipment for their use, provide a very sensitive method of detection. Those of ordinary skill in the art will know of other suitable labels which may be employed in accordance with the present invention. The binding of these labels to antibodies or fragments thereof may be accomplished using standard techniques (see, for example, Kennedy, et al. (1976) *Clin. Chim. Acta* 70:1-31 and Schurs, et al. (1977) *Clin. Chim Acta* 81:1-40).

In accordance with detecting the phosphorylation state of Tyr$^{644}$, the presence or absence of the antigen-antibody complex is correlated with phosphorylation of Tyr$^{644}$. For example, an agent which blocks the binding of an antibody which specifically recognizes phosphorylated Tyr$^{644}$, is indicative of an agent which blocks the phosphorylation of PIPKIγ661 by Src. Conversely, an agent which increases or stimulates, for example, the rate of phosphorylation of PIPKIγ661 by Src will increase or enhance the rate of binding of an antibody which specifically recognizes phosphorylated Tyr$^{644}$.

Another aspect of the present invention is a method for identifying an agent that modulates cell focal adhesion assembly. This cell-based assay involves contacting a cell which lacks active PIPKIγ661 or which overexpresses PIPKIγ661 with a test agent and measuring the adherence of the cell to a surface as compared to a same cell type which has not been contacted with the test agent. Agents which inhibit or decrease the adherence of a cell which overexpresses PIPKIγ661 are useful for treating conditions or diseases such as cancer invasiveness or cancer metastasis. Agents which increase, enhance, or stimulate adherence of a cell which lacks active PIPKIγ661 are useful for treating conditions or diseases involving wound healing, immune responses, or neuronal development. A cell which lacks active PIPKIγ661 may include a cell which expresses a kinase dead PIPKIγ661 or lacks expression of PIPKIγ661 either by using a gene knock out or inhibitory RNA approach. Promoters, vectors, and cell lines for expressing a PIPKIγ661, a kinase dead PIPKIγ661, or inhibitory RNA are provided herein. Methods of generating a cell line with a gene knock-out are well-known in the art.

Adherence of a cell to a surface (e.g., a membrane or petri plate) may be determined by washing experiments or by microscopic analysis. Washing experiments, for example, may be conducted by passing a medium over the cells on the surface and measuring the number of cells adhering in the presence and absence of a test agent. An increase in the number of cells which adhere in the presence of the agent is indicative of said agent enhancing or increasing cell adhesion. Conversely, an increase in the number of cells which do not adhere in the presence of the agent is indicative of said agent inhibiting or decreasing cell adhesion.

Alternatively, antibodies directed to focal adhesion proteins (e.g., PIPKIγ661 or talin) may be used to label focal adhesions in a determination of focal adhesion size. Overexpression of PIPKIγ661 increases the size of focal adhesions and, concurrently, the adherence of these cells. Hence, an agent which decreases the size of focal adhesions in a cell overexpressing PIPKIγ661, would accordingly decrease the adherence of the cell as well. Methods for observing focal adhesions in a cell are exemplified herein.

Agents which modulate the activity of PIPKIγ661 or cell focal adhesion assembly may be identified by screening a library of test agents. Agents are obtained from a wide variety of sources including libraries of synthetic or natural compounds. A library may comprise either collections of pure agents or collections of agent mixtures. Examples of pure agents include, but are not limited to, peptides, polypeptides, antibodies, oligonucleotides, carbohydrates, fatty acids, steroids, purines, pyrimidines, lipids, synthetic or semi-synthetic chemicals, and purified natural products, derivatives, structural analogs or combinations thereof. Examples of agent mixtures include, but are not limited to, extracts of prokaryotic or eukaryotic cells and tissues, as well as fermentation broths and cell or tissue culture supernates. In the case of agent mixtures, one may not only identify those crude mixtures that possess the desired activity, but also monitor purification of the active component from the mixture for characterization and development as a therapeutic drug. In particular, the mixture so identified may be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction may be assayed for the desired activity using the original assay until a pure, biologically active agent is obtained.

Agents of interest in the present invention are those with functional groups necessary for structural interaction with proteins, particularly hydrogen bonding, and typically include at least an amine, carbonyl, hydroxyl or carboxyl group, preferably at least two of the functional chemical groups. The agents often comprise cyclical carbon or heterocyclic structures and/or aromatic or polyaromatic structures substituted with one or more of the above functional groups.

Alternatively, peptide derivatives of the sequence of PIPKIγ661, PIPKIγ661 peptides PN, pY644, pY649, pY644/649, or talin may be designed to modulate the interaction between PIPKIγ661 and talin.

Agents which modulate the activity of PIPKIγ661 or cell focal adhesion assembly are useful as therapeutic agents for preventing or treating a cell migration-mediated condition or disease. Accordingly, another aspect of the present invention is a method for preventing or treating a cell migration-mediated condition or disease in a subject by administering to a subject an effective amount of an agent that modulates the activity of PIPKIγ661 or cell focal adhesion assembly in a cell lacking active PIPKIγ661 or overexpressing PIPKIγ661. Cell migration-mediated conditions or diseases which may be prevented or treated in accordance with the method of the invention include, but are not limited to, cancer invasiveness; cancer metastasis; wound healing; neuronal development (e.g., migration of axons in spinal cord injury); neuronal disorders (e.g., Hirschsprung's Disease); immune responses (e.g., macrophage migration); and immune disorders (e.g., Wiskott-Aldrich Syndrome). Whether the agent stimulates or enhances or inhibits or decreases the activity of PIPKIγ661 or cell focal adhesion assembly to provide a therapeutic effect will be dependent on the cell migration-mediated condition or disease. Preferably, an agent which stimulates or enhances the activity of PIPKIγ661 or cell focal adhesion assembly will be used to prevent or treat a condition or disease which has reduced cell migration or may benefit from a stimulation or enhancement of cell migration (e.g., in wound healing, neuronal development and immune responses). Further, it is preferable that an agent which inhibits or decreases the activity of PIPKIγ661 or cell focal adhesion assembly will be used to prevent or treat a condition or disease which has increased cell migration or may benefit from a decrease or inhibition of cell migration (e.g., cancer invasiveness or cancer metastasis).

A subject having, or at risk of having, a cell migration-mediated condition or disease may be treated in accordance with the method of the present invention. A subject at risk of having a cell migration-mediated condition or disease includes individuals who have a high probability of developing the condition or disease (e.g., metastasis of an existing cancer) or which may have inherited the condition or disease and may benefit from a preventive therapy.

An effective amount of an agent which modulates the activity of PIPKIγ661 or cell focal adhesion assembly is an amount which prevents, eliminates or alleviates at least one sign or symptom of a cell migration-mediated condition or disease. Signs or symptoms associated with a cell-migration-mediated condition or disease vary with the condition or disease being prevented or treated and are well-known to the skilled clinician. Examples of signs and/or symptoms of cancer metastasis that may be monitored to determine the effectiveness of an agent which modulates the activity of PIPKIγ661 or cell focal adhesion assembly include, but are not limited to, tumor size, feelings of weakness, and pain perception. The amount of the agent required to achieve the desired outcome of preventing, eliminating or alleviating a sign or symptom of a cell migration-mediated condition or disease will be dependent on the pharmaceutical composition of the agent, the patient and the condition of the patient, the mode of administration, and the type of condition or disease being prevented or treated.

A pharmaceutical composition is one which contains the agent and a pharmaceutically acceptable carrier. A pharmaceutically acceptable carrier is a material useful for the purpose of administering the medicament, which is preferably sterile and non-toxic, and may be solid, liquid, or gaseous materials, which is otherwise inert and medically acceptable, and is compatible with the active ingredients. A generally recognized compendium of methods and ingredients of pharmaceutical compositions is Remington: The Science and Practice of Pharmacy, Alfonso R. Gennaro, editor, 20th ed. Lippincott Williams & Wilkins: Philadelphia, Pa., 2000.

A pharmaceutical composition may contain other active ingredients such as preservatives. A pharmaceutical composition may take the form of a solution, emulsion, suspension, ointment, cream, granule, powder, drops, spray, tablet, capsule, sachet, lozenge, ampoule, pessary, or suppository. It may be administered by continuous or intermittent infusion, parenterally, intramuscularly, subcutaneously, intravenously, intra-arterially, intrathecally, intraarticularly, transdermally, orally, bucally, intranasally, as a suppository or pessary, topically, as an aerosol, spray, or drops, depending upon whether the preparation is used to treat an internal or external condition or disease. Such administration may be accompanied by pharmacologic studies to determine the optimal dose and schedule and would be within the skill of the ordinary practitioner.

An agent which modulates the activity of PIPKIγ661 or cell focal adhesion assembly and is useful as a therapeutic agent for preventing or treating a cell migration-mediated condition or disease may be identified using the screening assays provided herein or may also include agents which modulate the expression of PIPKIγ661 or talin. For example, the expression of PIPKIγ661 may be inhibited using inhibitory RNAs such as ribozymes, antisense RNA, RNAi, siRNA and the like. These RNA molecules may be designed to specifically interact with the nucleic acid sequences encoding PIPKIγ661 to decrease the expression of PIPKIγ661 thereby decreasing its capacity to bind to talin. As the RNA molecule encoding PIPKIγ661 is alternatively spliced and is unique from other PIPKIγ RNA molecules by containing exon 17, it is preferable that the inhibitory RNA molecule is directed to exon 17 of the gene encoding PIPKIγ661. Specific inhibitory RNA molecules may be selected experimentally or empirically. For example, siRNA target sites in exon 17 may be 19-27 nucleotides in length, include an AA dinucleotide sequence at the 5' end and preferably have a G/C content of 30-50% (see, e.g., Elbashir, et al. (2001) Nature 411: 494-498).

It is further contemplated that an agent which modulates the activity of PIPKIγ661 or cell focal adhesion assembly may be attached to a targeting moiety which delivers the agent to a cell-type or tissue of interest to decrease potentially harmful side-effects of modulating the activity of PIPKIγ661 or cell focal adhesion assembly in all cell-types or tissues. For example, a targeting moiety to a cancerous tumor may include peptide hormones such as bombesin, stomatostatin and luteinizing hormone-releasing hormone (LHRH) or analogs thereof. Cell-surface receptors for peptide hormones have been shown to be overexpressed in tumor cells (Schally (1994) Anti-Cancer Drugs 5:115-130; Lamharzi, et al. (1998) Int. J. Oncol. 12:671-675) and the ligands to these receptors are known tumor cell targeting agents (Grundker, et al. (2002) Am. J. Obstet. Gynecol. 187(3):528-37; WO 97/19954).

It is further contemplated that exogenous application or moderate overexpression of PIPKIγ661 may also have therapeutic value in treating or preventing a cell migration-mediated condition or disease.

The invention is described in greater detail by the following non-limiting examples.

EXAMPLE 1

Generation of Constructs

Site-directed mutagenesis for creation of kinase-dead PIPKIγ661 (D253A) was performed using PCR-primer overlap extension with mutagenic primers (Kunz, et al. (2000) supra). The mutagenic primers were 5'-CAA AAT GCA CCT TAA GTT CGC CCT CAA GGG CTC CAC-3' (SEQ ID NO:15) and 5'-GTA CGT GGA GCC CTT GAG GGC GAA CTT AAC CTG C-3' (SEQ ID NO:16). The flanking primers were 5'-CTA TGC ACC TGT TGC CTT CCG CTA CTT C-3' (SEQ ID NO:17) and 5'-GGC CGT GGA ATA CAG AGC CTT C-3' (SEQ ID NO:18). The mutation was confirmed by DNA sequence analysis. A 0.5-kilobase XmaI-ClaI restriction fragment was used to replace the corresponding restriction fragment in the HA-PIPKIγ661/pcDNA3 construct.

To construct PIPKIα/γ661 and PIPKIα/γ635 chimeras, a PmlI blunt cloning site was created after amino acid 444 of PIPKIα in pET28b (Novagen, Madison, WI) using well-established methods (Loijens and Anderson (1996) J. Biol. Chem. 271:32937-32943) with primers 5'-GCG TGA ACG GTT CAA GCG CTT CAC GTG CAA CAC AG-3' (SEQ ID NO:19) and 5'-CTT AAA TAC TGT GTT GAC CAT GAA GCG CTG G-3' (SEQ ID NO:20). The resulting construct was subsequently digested with PmlI and EcoRI. PIPKIγ661 and 635 C-terminal fragments (178 and 153 amino acids, respectively) were amplified by PCR from the corresponding HA-tagged pcDNA3 constructs, digested with EcoRI and ligated into the restricted PIPKIα pET28b vector. To construct the PIPKIα/γ26 chimera, a PmlI site was created immediately before the stop codon of PIPKIα in the pET28b using PCR primers 5'-CCC TTA AGC AGT GAA ACA CAG TAC TCA GTT G-3' (SEQ ID NO:21) and 5'-CCC CCA CGT GGG TGA ACT CTG ACT CTG-3' (SEQ ID NO:22). The resulting construct was then digested with PmlI and EcoRI. The PIPKIγ26 fragment was PCR amplified from the HA-tagged PIPKIγ661/pcDNA3 construct, digested and ligated into the PIPKIα vector described above. All three chimeras were then subcloned from pET28b into the pCMV TAG 3 (Stratagene, La Jolla, Calif.) mammalian expression vector and sequenced. GFPIγ26 was constructed by PCR amplification of the C-terminal 26 amino acids and 3'UTR of PIPKIγ661 with primer 5'-GCT CAA GCT TC<u>GAATTCT</u> CCC ACC GAC GAG AGG-3' (SEQ ID NO:23) and the vector primer SP6. An EcoRI site (underlined) was incorporated by PCR. The PCR product and EGFP vector was digested with EcoRI and ApaI. The GFPIγ26 construct was confirmed by sequencing.

Cloning of PIPKIγ661 into a bacterial expression vector was performed by liberating PIPKIγ661 from the HA-tagged PIPKIγ661 vector using SalI/NotI and subcloning into pET28c. The C-terminal 178 amino acid of PIPKIγ661 was obtained by PCR, digested with BamHI and EcoRI and subcloned into pET28c.

Human talin1 head region (1-435) was cloned from HEK293T cells by PCR and subcloned into pET42. The C-terminal truncated or site-directed mutagenesis for the PIPKIγ661 mutants or talin head was performed using PCR-primer overlap extension with mutagenic primers. PIPKIγ661 mutants were then subcloned into pcDNA3.1 and talin head mutants were subcloned into pET42. His-tagged mouse β1-integrin tail was made using well-established methods (Pfaff, et al. (1998) supra) and subcloned into pET28. The C-terminus of PIPKIγ635 (439-635), PIPKIγ661 (439-661), or the Tyr to Phe mutants of PIPKIγ661 were PCR amplified from the corresponding pcDNA3.1 constructs and subcloned into pET28. All mutants were confirmed by DNA sequence analysis. FAK, FAKTyr397Phe, kinase dead FAK and c-Src constructs were generated using well-known methods.

EXAMPLE 2

Yeast Two-hybrid Screen

The yeast two-hybrid screen was performed according to well-known methods (James, et al. (1996) *Genetics* 144: 1425-1436). cDNA libraries which were screened include mouse embryonic, human B cell, human breast, human prostate, human placenta and mouse brain.

EXAMPLE 3

Kinase Assays

Activity of purified recombinant or immunoprecipitated PIPKI proteins was assayed against 25 μM phosphotidylinositol-4-phosphate (PI4P) micelles using well-known methods (Kunz, et al. (2000) supra).

For in vitro Src kinase assays, primary chicken embryo (CE) cells were prepared and maintained as described (Reynolds (1987) *EMBO J.* 6:2359-2364). Exogenous c-SrcTyr527Phe was expressed using the RCAS B replication competent avian retroviral vector as described (Schaller, et al. (1999) supra; Reynolds (1987) supra). Cells were transfected with LIPOFECTAMINE™ (Life Technologies, Inc., Rockville, Md.) and LIPOFECTAMINE™ Plus (Life Technologies, Inc., Rockville, Md.) according to the manufacturer's instructions. Approximately 7-9 days post-transfection of RCAS B/c-Src, cells were lysed.

c-Src was immunoprecipitated from ~1 mg CE cell lysates using the EC10 monoclonal antibody and Protein A-SEPHAROSE (Amersham Pharmacia Biotech, Piscataway, N.J.) for 1 hour at 4° C. Immune complexes were washed twice with lysis buffer, twice with Tris-buffered saline (10 mM Tris-HCl, pH 7.5, 150 mM NaCl) and twice with kinase reaction buffer (20 mM PIPES, pH 7.2; 5 mM $MnCl_2$; 5 mM $MgCl_2$). The immune complexes were resuspended in kinase reaction buffer containing 35 μM ATP including 10 μCi of [γ-$^{32}$P] ATP (6000 Ci mmol$^{-1}$; Perkin Elmer LifeSciences, Boston, Mass.), and incubated with 4 μg of recombinant substrates for various times at room temperature. Reactions were terminated by adding sample buffer. Samples were resolved by SDS-PAGE and the gels then stained with SYPRO® Orange (Molecular Probes, Eugene, Oreg.) according to the manufacturer's instructions. The stained gels were analyzed for fluorescence and by phosphorimaging after drying, using a MOLECULAR DYNAMICS STORM® PHOSPHORIMAGER® (Sunnyvale, Calif.).

EXAMPLE 4

Cell Culture, Transfection, Immunofluorescence and Confocal Microscopy

HEK 293T cells and NRK cells were cultured in Dulbecco's modified Eagle's medium (DMEM) (Mediatech, Inc., Herndon, Va.) supplemented with 10% fetal bovine serum (INVITROGEN™, Carlsbad, Calif.) and antibiotics. NRK cells were transfected using FUGENE™ 6 (Roche, Indianapolis, Ind.) according to manufacturer's instructions for 24 hours. HEK293T cells in 1 μg/ml collagen-coated dishes were transfected using 2 μg PIP kinase expression vector together with 3-4 μg empty pcDNA3 vector, 3 μg CD2FAK or FRNK, 2 μg empty pcDNA3 vector plus 2 μg wild-type or mutant FAK, 2 μg empty pcDNA3 vector plus 2 μg c-Src, or 2 μg wild-type or mutant FAK plus 2 μg c-Src as indicated, using the well-known calcium phosphate-DNA coprecipitation method for 48 hours.

Immunofluorescence and confocal microscopy were performed as is well-known in the art (Kunz, et al. (2000) supra). Z series were created by sequentially scanning green and red channels at 0.2 μm steps.

EXAMPLE 5

Expression and Purification of PIP Kinase in *Escherichia coli* pET28 constructs containing His-tagged PIPKIα, PIPKIγ661, wild-type or mutant C-terminal tails of PIPKIγ661, β1-integrin tail, or pET42 constructs containing wild-type or mutant talin head regions were transformed into BL21(DE3) (Novagen, Inc., Madison, Wis.). Proteins were expressed and purified using His-resin following the manufacturer's instructions (Novagen, Inc., Madison, Wis.).

EXAMPLE 6

Antibodies

Anti-talin, anti-vinculin and anti-Flag (M2) antibodies were obtained from Sigma (St. Louis, Mo.). Monoclonal mouse anti-PY (4G10), anti-FAK (4.47), anti-Src (EC10) and anti-paxillin (5H11) were from Upstate Group, Inc. (Charlottesville, Va.). Polyclonal rabbit anti-PY antibody was obtained from Transduction Laboratories (Lexington, Ky.). Anti-HA and anti-c-Myc antibodies were from Covance (Harrogate UK). HRP-conjugated anti-GST antibody was obtained from Amersham Pharmacia Biotech (Piscataway, N.J.). Anti-His and HRP-conjugated anti-T7 antibodies were from INVITROGEN™ (Carlsbad, Calif.).

Polyclonal PIPKIγanti-serum was generated using purified His-tagged PIPKIγ661. Secondary antibodies were from Jackson Immunoresearch (West Grove, Pa.). Anti-serum was purified on an affinity column generated by coupling recombinant C-terminus of PIPKIγ661 to cyanogen bromide-activated Sepharose 4B (Sigma, St. Louis, Mo.) (Loijens and Anderson (1996) supra).

EXAMPLE 7

Immunoprecipitation and Immunoblotting

Immunoprecipitation was performed using standard methods (Zhang, et al. (1997) *J. Biol. Chem.* 272:17756-17761). Briefly, transfected HEK293T cells were harvested and lysed in Buffer A (50 mM Tris-HCl, pH 7.5, 150 mM NaCl, 0.1-1.0% NP-40, 5.0 mM NaF, 2 mM $Na_3VO_4$, 4 mM $Na_2P_2O_7$, 1 mM EDTA, 0.1 mM EGTA, 1 mM phenylmethyl sulphonyl fluoride (PMSF), 10% glycerol), centrifuged and incubated with protein A-Sepharose and 5 μg anti-HA, anti-c-Myc, anti-Flag, anti-PIPKIγor anti-talin antibody as indicated at 4° C. for 4 hours to overnight. The immunocomplexes were washed with Buffer A, separated by SDS-polyacrylamide gel electrophoresis (SDS-PAGE), and analyzed as indicated. For the kinase assay, the immunocomplexes were washed and stored in kinase buffer.

EXAMPLE 8

Cell Stimulation and Spreading

Transfected HEK 293T cells were washed with phosphate-buffer saline (PBS) and detached with 0.25% trypsin at 37° C. The cells were harvested and washed with PBS, and suspended in serum-free DMEM at 37° C. for 1 hour. After stimulation with 10 ng/ml platelet-derived growth factor (PDGF) (R&D Systems Inc., Minneapolis, Minn.), 1 μM LPA (Sigma, St. Louis) or serum at 37° C. for 15 minutes, cells were lysed as for immunoprecipitation. For spreading assays, transfected NRK cells were detached with 1 mM EDTA, washed with PBS, and subsequently $0.1 \times 10^6$ cells were plated on 1 μg/ml collagen-coated coverslips in serum-free DMEM. After the indicated time, the coverslips were fixed and stained as described herein.

EXAMPLE 9

Peptide Synthesis and GST Pull-down Assays

Phosphorylated or non-phosphorylated peptides relevant to PIPKIγ661, named as PN (Cys-Asp-Glu-Arg-Ser-Trp-Val-Tyr-Ser-Pro-leu-His-Tyr-Ser-Ala-Arg; SEQ ID NO:12), pY644 (Cys-Asp-Glu-Arg-Ser-Trp-Val-*Tyr-Ser-Pro-Leu-His-Tyr-Ser-Ala-Arg; SEQ ID NO:12), pY649 (Cys-Asp-Glu-Arg-Ser-Trp-Val-Tyr-Ser-Pro-Leu-His-*Tyr-Ser-Ala-Arg; SEQ ID NO:12), and pY644/649 (Cys-Asp-Glu-Arg-Ser-Trp-Val-*Tyr-Ser-Pro-Leu-His-*Tyr-Ser-Ala-Arg; SEQ ID NO:12)), wherein "*" indicates phosphorylation, were synthesized as >95% purity (INVITROGEN™, Carlsbad, Calif.). The peptides corresponding to β1-integrin tail, named as β1InPN (Cys-Met-Asn-Ala-Lys-Trp-Asp-Thr-Gly-Glu-Asn-Pro-Ile-Tyr-Lys-Ser-Ala; SEQ ID NO:14), β1InpT (Cys-Met-Asn-Ala-Lys-Trp-Asp-*Thr-Gly-Glu-Asn-Pro-Ile-Tyr-Lys-Ser-Ala; SEQ ID NO:14), β1InpY (Cys-Met-Asn-Ala-Lys-Trp-Asp-*Thr-Gly-Glu-Asn-Pro-Ile-*Tyr-Lys-Ser-Ala; SEQ ID NO:14), and β1InpTpY (Cys-Met-Asn-Ala-Lys-Trp-Asp-*Thr-Gly-Glu-Asn-Pro-Ile-*Tyr-Lys-Ser-Ala; SEQ ID NO:14), were synthesized as >97% purity (See http://biotech.wisc.edu/ServicesResearch/Peptide/PeptideSyn th/).

Purified GST-talin head proteins were incubated with PIPKIγ661 tails or β1-integrin tail, together with Glutathione SEPHAROSE™ 4 Fast Flow (Amersham Biosciences, Piscataway, N.J.), in Buffer B (PBS, 0.2% NP-40, 2 mM DTT) at 4° C. for 4 hours. The beads were washed three times with Buffer B and analyzed by western blot. For competition assays, GST-talin head proteins were incubated with peptides or competing proteins for 2 hours, then the binding proteins were added and the mixtures were incubated for another 4 hours.

What is claimed is:

1. A method for identifying an agent that modulates cell focal adhesion assembly comprising contacting a cell which lacks active PIPKIγ661 or which overexpresses PIPKIγ661 with a test agent and measuring the adherence of said cell to a surface, wherein a difference in the adherence of the cell to the surface in the presence of the test agent as compared to the adherence of the cell to the surface in the absence of the test agent is indicative of the agent modulating cell focal adhesion assembly.

* * * * *